(12) United States Patent
Kent et al.

(10) Patent No.: US 12,582,613 B2
(45) Date of Patent: Mar. 24, 2026

(54) BIOMIMETIC, REACTIVE OXYGEN SPECIES-DETONABLE NANOCLUSTERS FOR ANTIRESTENOTIC THERAPY

(71) Applicants: University of Virginia Patent Foundation, Charlottesville, VA (US); WISCONSIN ALUMNI RESEARCH FOUNDATION, Madison, WI (US)

(72) Inventors: Kenneth Craig Kent, Charlottesville, VA (US); Lian-Wang Guo, Madison, WI (US); Bowen Wang, Charlottesville, VA (US); Takuro Shirasu, Charlottesville, VA (US); Shaoqin Gong, Middleton, WI (US); Yi Zhao, Madison, WI (US)

(73) Assignees: University of Virginia Patent Foundation, Charlottesville, VA (US); WISCONSIN ALUMNI RESEARCH FOUNDATION, Madison, WI (US)

( * ) Notice: Subject to any disclaimer, the term of this patent is extended or adjusted under 35 U.S.C. 154(b) by 233 days.

(21) Appl. No.: 18/580,703

(22) PCT Filed: Jul. 21, 2022

(86) PCT No.: PCT/US2022/074011
§ 371 (c)(1),
(2) Date: Jan. 19, 2024

(87) PCT Pub. No.: WO2023/004387
PCT Pub. Date: Jan. 26, 2023

(65) Prior Publication Data
US 2024/0335392 A1    Oct. 10, 2024

Related U.S. Application Data

(60) Provisional application No. 63/224,466, filed on Jul. 22, 2021.

(51) Int. Cl.
| | |
|---|---|
| *A61P 9/14* | (2006.01) |
| *A61K 9/51* | (2006.01) |
| *A61K 31/517* | (2006.01) |

(52) U.S. Cl.
CPC .......... *A61K 9/5176* (2013.01); *A61K 9/5146* (2013.01); *A61K 31/517* (2013.01); *A61P 9/14* (2018.01)

(58) Field of Classification Search
CPC ............... A61K 9/5176; A61K 9/5146; A61K 31/517; A61K 35/19; A61K 9/0019;
(Continued)

(56) References Cited

U.S. PATENT DOCUMENTS

| | | |
|---|---|---|
| 10,370,391 B2 | 8/2019 | Kang et al. |
| 10,668,017 B2 | 6/2020 | Kent et al. |

(Continued)

FOREIGN PATENT DOCUMENTS

WO    WO-2019226963 A1 * 11/2019    ......... A61K 47/6935

OTHER PUBLICATIONS

Feng et al. (Biomaterials 2015;105:167-184) (Year: 2015).*

(Continued)

*Primary Examiner* — Ernst V Arnold
(74) *Attorney, Agent, or Firm* — Thomas I Horstemeyer, LLP

(57) ABSTRACT

In one aspect, the disclosure relates to nanoclusters comprising cores comprising self-assembled unimolecular nanoparticles and biomimetic membrane coatings surrounding the cores, methods of making the same, and methods of treating and preventing restenosis using same. In some embodiments, the nanoclusters can contain an anti-restenotic drug. In one embodiment, the polymers and/or copolymers of the unimolecular nanoparticles can contain a hydrophobic group such as, for example, a phenylboronic
(Continued)

ester. In a further embodiment, the biomimetic membrane can localize the nanoclusters at sites of vascular damage, at which time reactive oxygen species (ROS) at the sites of vascular damage cleave the hydrophobic groups from the polymers and/or copolymers, increasing hydrophilicity of the polymers and/or copolymers and allowing for greater tissue penetration of the de-clustered nanoclusters and nanoparticles.

17 Claims, 11 Drawing Sheets

Specification includes a Sequence Listing.

(58) Field of Classification Search
 CPC ................ A61K 9/5068; A61K 9/5153; A61K
  31/337; A61K 31/551; A61K 31/573;
  A61K 45/06; A61K 31/5517; A61P 9/14;
  A61P 9/00
 See application file for complete search history.

(56) References Cited

U.S. PATENT DOCUMENTS

| | | | |
|---|---|---|---|
| 11,446,392 B2 * | 9/2022 | Kent | .................... A61K 9/1075 |
| 12,161,726 B2 * | 12/2024 | Kent | .................... A61K 9/5068 |

OTHER PUBLICATIONS

Chen et al. (Acc Chem Res. May 2, 20191; 52(5): 1255-1264). (Year: 2019).*
Lv et al. (ACS Nano 2018;12:5417-5426). (Year: 2018).*
Lee et al. (Journal of Cerebrovascular and Endovascular Neurosurgery 2015;17(3): 217-222). (Year: 2015).*
Chen et al. (Biomacromolecules 2008, 9, 2578-2585) (Year: 2008).*
Ang, H. Y.; et al. Adventitial injection delivery of nano-encapsulated sirolimus (Nanolimus) to injury-induced porcine femoral vessels to reduce luminal restenosis. J. Control. Release 2020, 319, 15-24.
Anselmo, A.C.; et al. Nanoparticles in the clinic: An update. Bioengineering & Translational Medicine 2019, 4.
Bahnson, E. S. M.; et al. Targeted Nitric Oxide Delivery by Supramolecular Nanofibers for the Prevention of Restenosis After Arterial; InjuryAntioxid Redox Signal. Mar. 10, 2016;24(8):401-18. doi: 10.1089/ars.2015.6363. Epub Jan. 21, 2016. PMID: 26593400; PMCID: PMC4782035.
Banai, S.; et al. Targeted anti-inflammatory systemic therapy for restenosis: The Biorest Liposomal Alendronate with Stenting sTudy (BLAST)—a double blind, randomized clinical trial. Am. Heart J. 2013, 165, 234-240.
Barua, S.; et al. Challenges associated with penetration of nanoparticles across cell and tissue barriers: A review of current status and future prospects. Nano Today 2014, 9, 223-243.
Chan, J. M.; et al. In vivo prevention of arterial restenosis with paclitaxel-encapsulated targeted lipid-polymeric nanoparticles. Proceedings of the National Academy of Sciences 2011, 108, 19347-19352.
De Gracia Lux, C.; et al. Biocompatible Polymeric Nanoparticles Degrade and Release Cargo in Response to Biologically Relevant Levels of Hydrogen Peroxide. J. Am. Chem. Soc. 2012, 134, 15758-15764.
Fang, R. H.; et al. Cell Membrane Coating Nanotechnology. Adv. Mater. 2018, 30, 1706759.
Feng, L.; et al. Enhancement of Nanozyme Permeation by Endovascular Interventional Treatment to Prevent Vascular Restenosis via Macrophage Polarization Modulation. Adv. Funct. Mater. 2020, 30, 2006581.
Feng, S.; et al. Nanoparticles responsive to the inflammatory microenvironment for targeted treatment of arterial restenosis. Biomaterials 2016, 105, 167-184.
Hu, C. J.; et al. Nanoparticle biointerfacing by platelet membrane cloaking. Nature 2015, 526, 118-121.
Hu, Q.; et al. Anticancer Platelet-Mimicking Nanovehicles. Adv. Mater. 2015, 27, 7043-7050.
Iyer, R.; et al. Nanoparticle eluting-angioplasty balloons to treat cardiovascular diseases. Int. J. Pharmaceut. 2019, 554, 212-223.
Khoobchandani, M.; et al. Laminin Receptor-Avid Nanotherapeutic EGCg-AuNPs as a Potential Alternative Therapeutic Approach to Prevent Restenosis. Int. J. Mol. Sci. 2016, 17, 316.
Liu, X.; et al. Fusogenic Reactive Oxygen Species Triggered Charge-Reversal Vector for Effective Gene Delivery. Adv. Mater. 2016, 28, 1743-1752.
Margolis, J.; et al. Systemic Nanoparticle Paclitaxel (nab-Paclitaxel) for In-stent Restenosis I (SNAPIST-I): A First-in-Human Safety and Dose-finding Study. Clin. Cardiol. 2007, 30, 165-170.
Park, J. H.; et al. Biomimetic nanoparticle technology for cardiovascular disease detection and treatment. Nanoscale Horiz 2020, 5, 25-42.
Varshosaz, J.; et al. Magnetic chondroitin targeted nanoparticles for dual targeting of montelukast in prevention of in-stent restenosis. RSC Adv. 2016, 6, 12337-12347.
Wang, B.; et al. A paradigm of endothelium-protective and stent-free anti-restenotic therapy using biomimetic nanoclusters. Biomaterials 2018, 178, 293-301.
Wang, S.; et al. Drug Targeting via Platelet Membrane-Coated Nanoparticles. Small Structures 2020, 1, 2000018.
Yan, H.; et al. Engineering Cell Membrane-Based Nanotherapeutics to Target Inflammation. Advanced Science 2019, 6, 1900605.
Zein, R.; et al. Physical Properties of Nanoparticles That Result in Improved Cancer Targeting. Journal of Oncology 2020, 2020, 1-16.
Zhang, R.; et al. A pH/ROS dual-responsive and targeting nanotherapy for vascular inflammatory diseases. Biomaterials 2020, 230, 119605.
Zhao, Y.; et al. Biomimetic fibrin-targeted and H2O2-responsive nanocarriers for thrombus therapy. Nano Today 2020, 35, 100986.
Zhao, Y.; et al. Co-delivery of LOX-1 siRNA and statin to endothelial cells and macrophages in the atherosclerotic lesions by a dual-targeting core-shell nanoplatform: A dual cell therapy to regress plaques. J. Control. Release 2018, 283, 241-260.
Zhao, Y.; et al. Multifunctional Dextran Sulfate-Coated Reconstituted High Density Lipoproteins Target Macrophages and Promote Beneficial Antiatherosclerotic Mechanisms. Bioconjugate Chem. 2016, 28, 438-448.
Bingjie Gao, et al., "Polymer-Encapsulated Cobalt/ Gold Bimetallic Nanoclusters as Stimuli-Responsive Chemiluminescent Nanoprobes for Reactive Oxygen Species", ACS Publications, 2020,92,15, 10677-10685.
Huajie Zhua, et al., "Amultifunctional polymeric gene delivery system for circumventing biological barriers", J. Mater. Chem. B, 2019, 7, 384.
Yi Zhao, et al., "Hydrogen Peroxide-Responsive Platelet Membrane-Coated Nanoparticles for Thrombus Therapy", Biomater Sci. Apr. 7, 2021; 9(7) 2696-2708.
Yi Zhao, et al., "Biometric, ROS-detonable nanoclusters-A multimodal nanoplatform for anti-resenotic therapy", Journal of Controlled Release, vol. 338, 2021, 295-306.
PCT Search report in related PCT Application No. PCT/US2022/074011, mailed Dec. 15, 2022.

* cited by examiner

Without H₂O₂                    With H₂O₂

```
                              SEQUENCE LISTING

Sequence total quantity: 14
SEQ ID NO: 1                moltype = DNA  length = 25
FEATURE                     Location/Qualifiers
source                      1..25
                            mol_type = other DNA
                            organism = synthetic construct
SEQUENCE: 1
actgtgtacg tggatgtgct caaag                                          25

SEQ ID NO: 2                moltype = DNA  length = 21
FEATURE                     Location/Qualifiers
source                      1..21
                            mol_type = other DNA
                            organism = synthetic construct
SEQUENCE: 2
cacgctgtcc cagttgtcaa g                                              21

SEQ ID NO: 3                moltype = DNA  length = 21
FEATURE                     Location/Qualifiers
source                      1..21
                            mol_type = other DNA
                            organism = synthetic construct
SEQUENCE: 3
attccaccca tggcaaattc c                                              21

SEQ ID NO: 4                moltype = DNA  length = 20
FEATURE                     Location/Qualifiers
source                      1..20
                            mol_type = other DNA
                            organism = synthetic construct
SEQUENCE: 4
gactccacga cgtactcagc                                                20

SEQ ID NO: 5                moltype = DNA  length = 20
FEATURE                     Location/Qualifiers
source                      1..20
                            mol_type = other DNA
                            organism = synthetic construct
SEQUENCE: 5
cttccaagtg gctaagggca                                                20

SEQ ID NO: 6                moltype = DNA  length = 20
FEATURE                     Location/Qualifiers
source                      1..20
                            mol_type = other DNA
                            organism = synthetic construct
SEQUENCE: 6
tcaaagggag tcggggatct                                                20

SEQ ID NO: 7                moltype = DNA  length = 20
FEATURE                     Location/Qualifiers
source                      1..20
                            mol_type = other DNA
                            organism = synthetic construct
SEQUENCE: 7
gatcggtccc aacaaggagg                                                20

SEQ ID NO: 8                moltype = DNA  length = 20
FEATURE                     Location/Qualifiers
source                      1..20
                            mol_type = other DNA
                            organism = synthetic construct
SEQUENCE: 8
tccctcaggg gtgtccttag                                                20

SEQ ID NO: 9                moltype = DNA  length = 20
```

-continued

```
FEATURE             Location/Qualifiers
source              1..20
                    mol_type = other DNA
                    organism = synthetic construct
SEQUENCE: 9
cactaaagtg cccgagctga                                                    20

SEQ ID NO: 10       moltype = DNA  length = 20
FEATURE             Location/Qualifiers
source              1..20
                    mol_type = other DNA
                    organism = synthetic construct
SEQUENCE: 10
tccagatggt gagtgaggca                                                    20

SEQ ID NO: 11       moltype = DNA  length = 20
FEATURE             Location/Qualifiers
source              1..20
                    mol_type = other DNA
                    organism = synthetic construct
SEQUENCE: 11
actggaatgt cagctcgcaa                                                    20

SEQ ID NO: 12       moltype = DNA  length = 20
FEATURE             Location/Qualifiers
source              1..20
                    mol_type = other DNA
                    organism = synthetic construct
SEQUENCE: 12
tcaaattccg tggccacctt                                                    20

SEQ ID NO: 13       moltype = DNA  length = 20
FEATURE             Location/Qualifiers
source              1..20
                    mol_type = other DNA
                    organism = synthetic construct
SEQUENCE: 13
gacatgccgc ctggagaaac                                                    20

SEQ ID NO: 14       moltype = DNA  length = 20
FEATURE             Location/Qualifiers
source              1..20
                    mol_type = other DNA
                    organism = synthetic construct
SEQUENCE: 14
agcccaggat gccctttagt                                                    20
```

BIOMIMETIC, REACTIVE OXYGEN SPECIES-DETONABLE NANOCLUSTERS FOR ANTIRESTENOTIC THERAPY

CROSS REFERENCE TO RELATED APPLICATIONS

This application is a U.S. national phase application under 35 U.S.C. 371 of International Patent Application No. PCT/US22/74011, filed on Jul. 21, 2022, which claims the benefit of U.S. Provisional Application No. 63/224,466 filed on Jul. 22, 2021, which is incorporated herein by reference in its entirety.

STATEMENT REGARDING FEDERALLY SPONSORED RESEARCH OR DEVELOPMENT

This invention was made with government support under grant numbers R01 HL-129785, R01HL-133665, and R01HL-143469 awarded by the National Heart, Lung, and Blood Institute of the National Institutes of Health. The government has certain rights in the invention.

CROSS REFERENCE TO SEQUENCE LISTING

The genetic components described herein are referred to by sequence identifier numbers (SEQ ID NO.). The Sequence Listing, filed in electronic form as an xml file entitled 222117_2130_Sequence_Listing.xml in written computer readable format (CRF) having file size 13.0 kilobytes, created on Jul. 12, 2022, is incorporated by reference in its entirety.

BACKGROUND

Cardiovascular disease is the number one cause of death in developed countries. Endovascular intervention strategies such as angioplasty and stenting remain the gold standard to reconstruct occluded vessels. Unfortunately, these reconstructed vessels will re-occlude over time; this re-occlusion is referred to as restenosis. Restenosis occurs primarily due to the formation of neointima in the vessel wall, a process termed intimal hyperplasia (IH) featuring the overproliferation and phenotypic transformation of vascular smooth muscle cells (VSMC).

Drug-eluting stents (DES) and drug-coated balloons (DCB) are currently the standard of care for restenosis. However, they do not completely prevent IH and, in fact, worsen thrombogenic risks. In-stent restenosis occurs in ~10-23% of coronary DES applications, and up to 75% of those placed in the peripheral vasculature. Moreover, stent thrombosis has become a chief concern, as it causes sudden death in up to 40% of those patients. Increasing evidence reveals that the permanent presence of metal stents leads to sustained mechanical injury and hemodynamic disturbance, which ultimately nurtures a pro-restenotic and pro-thrombogenic local endovascular milieu. Therefore, the ultimate outcome of DES implantation for restenosis prevention, paradoxically, can be the persistence of in-stent restenosis and exacerbated thrombogenic risks. To address the downsides of DES, alternative stent-free strategies such as drug-eluting balloons and absorbable stents have been clinically assessed. However, recent studies have demonstrated increased mortality and significant safety concerns associated with these alternatives, and Food and Drug Administration (FDA) has since issued multiple warnings. Therefore, there is a clear and pressing clinical need for a stent-free anti-restenotic therapy.

In recent years, nanomedicine has been considered as a promising solution for targeted drug delivery in cardiovascular applications. In the case of anti-restenotic therapy, various types of drug nanocarriers have been documented, including inorganic, polymeric, liposomal nanoparticles, etc. Biointerfacing with cell membrane coatings is an emerging concept in precision medicine, which can facilitate drug delivery via integrating the biomimetic features of cell membrane with the versatile functions of nanocores. Platelets are of particular relevance to endovascular interventions. Upon angioplasty or other endovascular injuries, platelet can autonomously home to the lesional vessel through the interaction between platelet membrane surface proteins (e.g., glycoprotein VI) and the exposed sub-endothelial matrix in the vessel wall. Indeed, several studies have demonstrated the feasibility of platelet-inspired biomimetic coating in improving nanoparticle performances, including lesion-targeting property after angioplasty. However, other "lesion-responder" cell types such as, for example, macrophages, leukocytes, endothelial cells, endothelial progenitor cells, and/or mesenchymal stem cells may share similar properties.

In addition to lesion targetability, the ideal drug delivery system should also encompass enhanced tissue penetrability. The tissue penetration capacity of existing nanoplatforms is often suboptimal for cardiovascular applications. Unlike the "leaky," thin-layered microvasculature in the case of tumor, the major arterial and aortic vessels are contain multilayered smooth muscle, elastic laminae, and significant amount of extracellular matrix (ECM)—all of which impede the penetration of nanoparticles and hence the delivery of therapeutic payloads. This is particularly concerning in diseased vasculatures, where IH and ECM over-accumulation mount extra physical barricade to nanoparticle infiltration. It is increasingly recognized that particle size plays a vital role in its biodistribution and tissue penetration, yet oftentimes these two features are not attainable simultaneously. Nanoparticles with a size ranging between 100 to 200 nm typically possess longer circulation time due to less sequestration in spleen and liver, but their tissue penetration capacity is somewhat limited. In contrast, smaller-sized nanoparticles offer much deeper penetration. Therefore, an ideal delivery system should have an initial size ranging from 100-200 nm to achieve longer circulation time, but it may be switched to smaller particle size once reaching in the target lesions to facilitate tissue penetration for more efficient drug delivery.

Despite advances in anti-restenotic application research, there is still a scarcity of methods that have vascular lesion-targeting properties while remaining biocompatible, that are tunable in size for optimal balance between biodistribution and tissue penetration, and that allow for high drug loading capacity as well as controlled release. These needs and other needs are satisfied by the present disclosure.

SUMMARY

In accordance with the purpose(s) of the present disclosure, as embodied and broadly described herein, the disclosure, in one aspect, relates to nanoclusters comprising unimolecular nanoparticles with self-assembled cores and biomimetic membrane coatings surrounding the cores, methods of making the same, and methods of treating and preventing restenosis using same. In some embodiments, the nanoclusters can contain an anti-restenotic drug. In one embodiment, the polymers and/or copolymers of the unimolecular nanoparticles can contain a hydrophobic group such as, for example, a phenylboronic ester. In a further embodiment, the biomimetic membrane can localize the nanoclusters at sites of vascular damage, at which time reactive oxygen species (ROS) at the sites of vascular damage cleave the hydrophobic groups from the polymers and/or copolymers, increasing hydrophilicity of the polymers and/or copolymers and allowing for better tissue penetration of the de-clustered nanoclusters.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A: Schematic illustration for the $H_2O_2$-triggered detonation of the nanocluster. FIG. 1B: Size distribution measured by dynamic light scattering (DLS) and digital photos of the nanoclusters (Left) and de-clustered, unimolecular nanoparticles (Right) in response to stimulation with 100 µM $H_2O_2$. FIG. 1C: Transmission electron microscope (TEM) images of the nanoclusters in response to 100 µM $H_2O_2$. FIG. 1D: Drug release kinetics from the biomimetic nanoparticles in PBS (0.1 M, pH 7.4) with or without 100 µM $H_2O_2$. Data are presented as mean±SEM (n=3).

FIG. 2A: Determining the cytotoxicity profile of the platelet membrane-coated, ROS-detonable nanocluster. At different time points after exposing confluent VSMC to various concentrations (from to 10 ng/mL to 300 µg/mL) of the nanoclusters, cell viability was measured using CellTiter-Glo Luminescent Cell Viability assay. Data are presented as mean±SEM (n=3). FIGS. 2B-2C: Evaluating the anti-proliferative and APOA-1-inducing performances of an anti-restenotic drug (RVX) delivered through the innovative nanoclusters. 20 ng/mL platelet-derived growth factor-BB (PDGF-BB) was used to induce the proliferation of VSMC. In the RVX containing formulations-treated groups (i.e., free RVX, RVX-loaded nanoclusters (NC), and RVX-loaded poly(lactic-co-glycolic acid) (PLGA) NP), PDGF-BB-stimulated cells were treated with various formulations at an equivalent amount of RVX (1 µM or 10 µM). At 24, 48, 72, and 96 h post-treatment, the cell proliferation activity was measured by a CellTiter-Glo Luminescent kit. Additionally, additional sets of VSMC were subject to mRNA isolation at 48 h post-treatment followed by qPCR evaluation of APOA-I mRNA levels. Data are presented as mean±SEM (n=4). *P<0.05, P<0.01, *P<0.001. In FIG. 2B, statistical significances were marked between RVX-loaded NC and RVX-loaded PLGA NP. One-Way ANOVA followed by post-hoc Bonferroni analysis.

FIG. 3A: Ex vivo fluorescence images of the balloon-injured and non-injured carotid arteries. Cy5.5-loaded PLGA NP and Cy5.5-loaded NC were intravenously injected immediately after balloon angioplasty of the rat carotid artery. The balloon-injured and non-injured carotid arteries were collected 24 h later for ex vivo imaging using a IVIS system (Ex/Em: 676/705 nm). I and N represent the injured and non-injured carotid artery. FIG. 3B: Ex vivo fluorescence images of the Cy5.5-loaded PLGA NP and Cy5.5-loaded NC in the major organs and injured and non-injured carotid arteries. H, L, S, Lu, K, In, I and N represent heart, liver, spleen, lung, kidney, intestine, injured artery, and non-injured artery, respectively. FIG. 3C: Quantitative analysis of the mean fluorescence intensity per unit mass in each organ or tissue shown in the ex vivo images. Data are presented as mean±SEM (n=3). *P<0.05 and **P<0.01. One-Way ANOVA followed by post-hoc Bonferroni analysis.

FIG. 5A: H&E stained histological sections of balloon-injured carotid arteries after various treatments. Scale bars: 100 µm for 10× low magnification fields, and 50 µm for 40× high magnification fields. Saline, free RVX, empty NC, RVX-loaded PLGA NP, and RVX-loaded NC were injected via tail vein immediately after balloon angioplasty. Two-weeks later, the injured carotid arteries were excised, sliced, and stained with H&E for histopathological analysis. FIG. 5B: Quantitative analysis of the I/M ratio and lumen area. Data are presented as mean±SEM (n=4-6). *P<0.05 and **P<0.01. One-Way ANOVA followed by post-hoc Bonferroni analysis.

FIG. 6A: A schematic description of the preparation and detonation of the nanocluster. First, multiple small unimolecular nanoparticles self-assemble to form the nanocluster structure in aqueous solution via the hydrophobic interaction between phenylboronic esters. Subsequently, platelet membrane is coated on the surface of the nanoclusters via an extrusion process to confer lesion-targetability and particle stability in aqueous solution. After homing to the restenotic vessels that are highly enriched with ROS, the ROS-detonable nanoclusters will de-cluster to smaller hydrophilic unimolecular nanoparticles and penetrate the multilayered vessel wall structure, thus allowing the effective delivery of anti-restenotic payloads to the "epicenter" of endovascular lesion. FIG. 6B: Synthesis scheme of the unimolecular nanoparticles. H40-OH is used as a macromolecular initiator to synthesize H40-PLA-OH (Polymer 1, where PLA is polylactic acid) by ring-opening polymerization of D,L-lactide monomer. A bromide initiator (Polymer 2) for atom transfer radical polymerization (ATRP) can be synthesized through esterification. Thereafter, H40-PLA-P(tBMA-co-DMAEMA) (Polymer 3, where DMAEMA is dimethylaminoethyl acrylate) can be synthesized via ATRP. The final product used to form the $H_2O_2$-responsive unimolecular nanoparticles (H40-PLA-P(MAA-co-(DMAEMA-PAPE)), Polymer 4, where PMAA is poly(methacrylic acid)) can be prepared through conjugation of hydrophobic phenylboronic ester followed by deprotection of tert-butyl alcohol. Upon sensing the elevated $H_2O_2$ at the restenosis site, the hydrophobic phenylboronic ester will be rapidly oxidized and cleaved to form hydrophilic unimolecular nanoparticles.

Figure 1A:
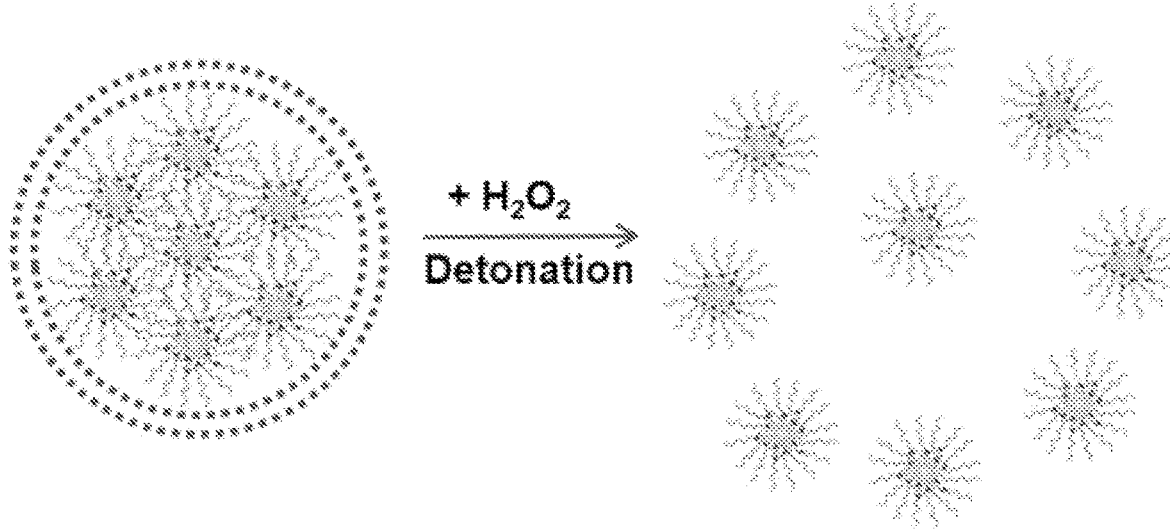
FIGS. 1A-1D show characterization of platelet membrane-coated, ROS-detonable nanoclusters.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Disclosed herein are nanoclusters including at least (a) a core containing self-assembled unimolecular nanoparticles, wherein the core, upon exposure to at least one reactive oxygen species (ROS), disassembles back into unimolecular nanoparticles; and (b) a biomimetic membrane coating surrounding the core. In one aspect, the membrane can be a platelet-derived membrane, a macrophage-derived membrane, a leukocyte-derived membrane, a mesenchymal stem cell-derived membrane, an exosomal membrane, a liposomal membrane, or any combination thereof. In one aspect, the biomimetic membrane is derived from human cells such as, for example, platelets, macrophages, leukocytes, mesenchymal stem cells, endothelial cells, or endothelial progenitor cells, or from exosomes or liposomes. Exemplary methods for deriving a membrane from a cell are provided in the Examples.

In one aspect, the unimolecular nanoparticles include a hydrophobic group such as, for example, a phenylboronic ester. In a further aspect, the unimolecular nanoparticles include a polymer or copolymer having units derived from a lactide monomer. In one aspect, the copolymer can be a block copolymer such as, for example, H40-polylactide-block-poly{methacrylic acid-ran-2-(methacryloyloxy)-N,N-dimethyl-N-[4-(4,4,5,5-tetramethyl-1,3,2-dioxaborolan-2-yl)benzyl]ethan-1-aminium}.

In another aspect, the nanocluster includes a drug such as, for example, an anti-restenotic drug. In one aspect, the anti-restenotic drug can be RVX-208, RVX-297, resveratrol, JQ1, OTX-015, ZEN-3694, I-BET762, ABBV-744, ARV-825, sirolimus, everolimus, tacrolimus, paclitaxel, GCN2-IN-1 (A-92), GSK2606414, GSK2656157, halofuginone, CI-amidine, D-CI-amidine, CI4-amidine, CAY10723, GSK484, EZP-6438, A-395, EED226, tubastatin, SIS3, centrinone B, or any combination thereof.

In one aspect, the unimolecular nanoparticles have an average diameter of from about 10 nm to about 70 nm, or of about 10, 15, 20, 25, 30, 35, 40, 45, 50, 55, 60, 65, or about 70 nm, or a combination of any of the foregoing values, or a range encompassing any of the foregoing values.

Also disclosed herein are compositions including a plurality of individual nanoclusters as disclosed herein. In one aspect, the individual nanoclusters can have an average diameter of from about 100 nm to about 250 nm, or of about 100, 110, 120, 130, 140, 150, 160, 170, 180, 190, 200, 210, 220, 230, 240, or about 250 nm, or a combination of any of the foregoing values, or a range encompassing any of the foregoing values.

Furthermore, disclosed herein is a method for making a nanocluster composition, the method including at least the steps of: (a) polymerizing a hydrophobic biodegradable polymer or copolymer including units derived from at least one monomer, wherein the polymer or copolymer further includes a hydroxyl end group; (b) functionalizing the hydrophobic biodegradable polymer or copolymer with at least one anionic functional group and with at least one cationic functional group; (c) functionalizing the cationic functional group with a hydrophobic end group; (d) preparing unimolecular nanoparticles from the hydrophobic biodegradable polymer or copolymer, wherein the unimolecular nanoparticles self-assemble into uncoated nanoclusters; and (e) extruding a biomimetic membrane derived from liposomes, exosomes, or at least one lesion-responder cell type onto the uncoated nanoclusters to form a nanocluster composition.

In one aspect, the monomer can be lactide, valerolactone, glycolide, caprolactone, a derivative thereof, or any combination thereof. In another aspect, the lesion-responder cell type can be platelets, macrophages, leukocytes, mesenchymal stem cells, endothelial cells, endothelial progenitor cells, or any combination thereof.

In another aspect, the at least one anionic functional group can be a carboxyl group, a sulfo group, a phosphate group, or any combination thereof. In still another aspect, the at least one cationic functional group can be a primary amine, a secondary amine, a tertiary amine, or any combination thereof.

In another aspect, in the disclosed method, the hydrophilic biodegradable polymer or copolymer is admixed with a drug prior to or during step (d). In a further aspect, the drug can be RVX-208, RVX-297, resveratrol, JQ1, OTX-015, ZEN-3694, I-BET762, ABBV-744, ARV-825, sirolimus, everolimus, tacrolimus, paclitaxel, GCN2-IN-1 (A-92), GSK2606414, GSK2656157, halofuginone, CI-amidine, D-CI-amidine, CI4-amidine, CAY10723, GSK484, EZP-6438, A-395, EED226, tubastatin, SIS3, centrinone B, or any combination thereof. In any of these aspects, the hydrophobic end group can be a phenylboronic ester.

In one aspect, disclosed herein is a nanocluster composition manufactured using the disclosed method. In some aspects, the nanocluster composition is biodegradable.

Also disclosed herein is a method for treating or preventing at least one vascular damage event in a subject, the method including administering a disclosed nanocluster composition to the subject. In another aspect, the biomimetic membrane localizes the nanoclusters at one or more sites of vascular damage in the subject. In some aspects, the at least one vascular damage event can be restenosis, aneurysm, deep vein thrombosis, or any combination thereof.

In one aspect, administering the nanocluster composition is accomplished by intravenous injection. In one aspect, the nanocluster composition is administered at a dosage such that the subject receives from about 5 to about 50 mg of the drug per kg of body weight of the subject, or about 10 mg of the drug per kg of body weight, or about 5, 10, 15, 20, 25, 30, 35, 40, 45, or about 50 mg of the drug per kg of body weight, or a combination of any of the foregoing values, or a range encompassing any of the foregoing values.

In another aspect, the drug can be selected from RVX-208, RVX-297, resveratrol, JQ1, OTX-015, ZEN-3694, I-BET762, ABBV-744, ARV-825, sirolimus, everolimus, tacrolimus, paclitaxel, GCN2-IN-1 (A-92), GSK2606414, GSK2656157, halofuginone, CI-amidine, D-CI-amidine, CI4-amidine, CAY10723, GSK484, EZP-6438, A-395, EED226, tubastatin, SIS3, centrinone B, or any combination thereof. In one aspect, the nanocluster composition is administered once, or is administered as needed. In a further aspect, the disclosed nanocluster compositions enable administration of lower doses of drugs than direct administration of the drugs. For example, a current treatment may require 50 to 150 mg of drug per kg of subject body weight to be administered twice a day, while the disclosed compositions reduce both the dosage and dosage frequency while retaining effectiveness.

In another aspect, in the disclosed method, one or more reactive oxygen species at the one or more sites of vascular damage cleaves the hydrophobic end group, wherein cleavage of the hydrophobic end group triggers release of one or more water soluble byproducts and a transition of the unimolecular nanoparticles to hydrophilic nanoparticles. In any of these aspects, the subject can be a human.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by," "comprising," "comprises," "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used herein, "biomimetic membrane" refers to a membrane coating for a polymeric core, wherein the membrane coating is derived from a cellular membrane. In one aspect, biomimetic membranes are biocompatible and non-toxic, and will not generate an immune response when used to treat patients. Biomimetic membranes can be derived from platelets, macrophages, and/or leukocytes using procedures described in the Examples.

As used in the specification and the appended claims, the singular forms "a," "an" and "the" include plural referents unless the context clearly dictates otherwise. Thus, for example, reference to "a drug," "a polylactide," or "an ROS-responsive polymer," includes, but is not limited to, mixtures or combinations of two or more such drugs, polylactides, or ROS-responsive polymers, and the like.

As used herein, the terms "treating" and "treatment" can refer generally to obtaining a desired pharmacological and/or physiological effect. The effect can be, but does not necessarily have to be, prophylactic in terms of preventing or partially preventing a disease, symptom, or condition thereof, such as restenosis. The effect can be therapeutic in terms of a partial or complete cure of a disease, condition, symptom, or adverse effect attributed to the disease, disorder, or condition. The term "treatment" as used herein can include any treatment of restenosis and/or vascular damage in a subject, particularly a human, and can include any one or more of the following: (a) preventing the damage from occurring in a subject who may be predisposed to the condition but has not yet been diagnosed as having it; (b) inhibiting the condition, i.e., arresting its development; and (c) relieving the condition, i.e., mitigating or ameliorating the disease and/or its symptoms. The term "treatment" as used herein can refer to both therapeutic treatment alone, prophylactic treatment alone, or both therapeutic and pro- phylactic treatment.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y.' The range can also be expressed as an upper limit, e.g. 'about x, y, z, or less' and should be interpreted to include the specific ranges of 'about x,' 'about y', and 'about z' as well as the ranges of 'less than x', less than y', and 'less than z'. Likewise, the phrase 'about x, y, z, or greater' should be interpreted to include the specific ranges of 'about x,' 'about y,' and 'about z' as well as the ranges of 'greater than x,' greater than y,' and 'greater than z.' In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 0.5% to about 2.4%;

about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

Unless otherwise specified, temperatures referred to herein are based on atmospheric pressure (i.e. one atmosphere).

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

ASPECTS

The following list of exemplary aspects supports and is supported by the disclosure provided herein.

Aspect 1. A nanocluster comprising:

(a) a core comprising self-assembled unimolecular nanoparticles, wherein the core, upon exposure to at least one reactive oxygen species (ROS), disassembles back into unimolecular nanoparticles; and (b) a biomimetic membrane coating surrounding the core.

Aspect 2. The nanocluster of aspect 1, wherein the biomimetic membrane comprises a platelet-derived membrane, a macrophage-derived membrane, a leukocyte-derived membrane, a mesenchymal stem cell-derived membrane, an exosomal membrane, a liposomal membrane, or any combination thereof.

Aspect 3. The nanocluster of aspect 1 or 2, wherein the unimolecular nanoparticles comprise a hydrophobic group.

Aspect 4. The nanocluster of aspect 3, wherein the hydrophobic group comprises a phenylboronic ester.

Aspect 5. The nanocluster of any one of aspects 1-4, wherein the unimolecular nanoparticles comprise a polymer or copolymer comprising units derived from a lactide monomer.

Aspect 6. The nanocluster of aspect 5, wherein the copolymer comprises a block copolymer.

Aspect 7. The nanocluster of aspect 6, wherein the block copolymer comprises H40-polylactide-block-poly{methacrylic acid-ran-2-(methacryloyloxy)-N,N-dimethyl-N-[4-(4,4,5,5-tetramethyl-1,3,2-dioxaborolan-2-yl)benzyl]ethan-1-aminium}.

Aspect 8. The nanocluster of any one of the preceding aspects, wherein the biomimetic membrane coating is derived from human cells, exosomes, or liposomes.

Aspect 9. The nanocluster of aspect 8, wherein the human cells comprise platelets, macrophages, leukocytes, mesenchymal stem cells, endothelial cells, or endothelial progenitor cells.

Aspect 10. The nanocluster of any one of the preceding aspects, further comprising a drug.

Aspect 11. The nanocluster of aspect 10, wherein the drug comprises an anti-restenotic drug.

Aspect 12. The nanocluster of aspect 11, wherein the anti-restenotic drug comprises RVX-208, RVX-297, resveratrol, JQ1, OTX-015, ZEN-3694, I-BET762, ABBV-744, ARV-825, sirolimus, everolimus, tacrolimus, paclitaxel, GCN2-IN-1 (A-92), GSK2606414, GSK2656157, halofuginone, CI-amidine, D-CI-amidine, CI4-amidine, CAY10723, GSK484, EZP-6438, A-395, EED226, tubastatin, SIS3, centrinone B, or any combination thereof.

Aspect 13. The nanocluster of any one of the preceding aspects, wherein the unimolecular nanoparticles have an average diameter of from about 10 to about 70 nm.

Aspect 14. A nanocluster composition comprising a plurality of individual nanoclusters according to any one of the preceding aspects.

Aspect 15. The nanocluster composition of aspect 14, wherein the individual nanoclusters have an average diameter of from about 100 to 250 nm.

Aspect 16. A method for making a nanocluster composition comprising:
  (a) polymerizing a hydrophobic biodegradable polymer or copolymer comprising units derived from at least one monomer, wherein the polymer or copolymer further comprises a hydroxyl end group;
  (b) functionalizing the hydrophobic biodegradable polymer or copolymer with at least one anionic functional group and with at least one cationic functional group;
  (c) functionalizing the cationic functional group with a hydrophobic end group;
  (d) preparing unimolecular nanoparticles from the hydrophobic biodegradable polymer or copolymer, wherein the unimolecular nanoparticles self-assemble into uncoated nanoclusters;
  (e) extruding a biomimetic membrane derived from liposomes, exosomes, or at least one lesion-responder cell type onto the uncoated nanoclusters to form a nanocluster composition.

Aspect 17. The method of aspect 16, wherein the monomer comprises lactide, valerolactone, glycolide, caprolactone, a derivative thereof, or any combination thereof.

Aspect 18. The method of aspect 16 or 17, wherein the lesion-responder cell type comprises platelets, macrophages, leukocytes, mesenchymal stem cells, or any combination thereof.

Aspect 19. The method of any one of aspects 16-18, wherein the at least one anionic functional group comprises a carboxyl group, a sulfo group, a phosphate group, or any combination thereof.

Aspect 20. The method of any one of aspects 16-19, wherein the at least one cationic functional group comprises a primary amine, a secondary amine, a tertiary amine, or any combination thereof.

Aspect 21. The method of any one of aspects 16-20, further comprising admixing the hydrophobic biodegradable polymer or copolymer with a drug prior to or during step (d).

Aspect 22. The method of aspect 21, wherein the drug comprises RVX-208, RVX-297, resveratrol, JQ1, OTX-015, ZEN-3694, I-BET762, ABBV-744, ARV-825, sirolimus, everolimus, tacrolimus, paclitaxel, GCN2-IN-1 (A-92), GSK2606414, GSK2656157, halofuginone, CI-amidine, D-CI-amidine, CI4-amidine, CAY10723, GSK484, EZP-6438, A-395, EED226, tubastatin, SIS3, centrinone B, or any combination thereof.

Aspect 23. The method of any one of aspects 16-22, wherein the hydrophobic end group comprises a phenylboronic ester.

Aspect 24. A nanocluster composition manufactured using the method of any one of aspects 16-23.

Aspect 25. The nanocluster composition of any one of aspects 14, 15, or 24, wherein the nanocluster composition is biocompatible.

Aspect 26. A method for treating or preventing at least one vascular damage event in a subject, the method comprising administering the nanocluster composition of any one of aspects 14, 15, 24, or 25 to a subject.

Aspect 27. The method of aspect 26, wherein the biomimetic membrane localizes the nanoclusters at one or more sites of vascular damage in the subject.

Aspect 28. The method of aspect 26 or 27, wherein the at least one vascular damage event comprises restenosis, aneurysm, deep vein thrombosis, or any combination thereof.

Aspect 29. The method of any one of aspects 26-28, wherein administering the nanocluster composition comprises intravenous injection.

Aspect 30. The method of any one of aspects 26-29, wherein the nanocluster composition comprises from about 5 to about 50 mg of a drug per kg of body weight of the subject.

Aspect 31. The method of any one of aspects 26-29, wherein the nanocluster composition comprises about 10 mg of a drug per kg of body weight of the subject.

Aspect 32. The method of aspect 30 or 31, wherein the drug comprises RVX-208, RVX-297, resveratrol, JQ1, OTX-015, ZEN-3694, I-BET762, ABBV-744, ARV-825, sirolimus, everolimus, tacrolimus, paclitaxel, GCN2-IN-1 (A-92), GSK2606414, GSK2656157, halofuginone, CI-amidine, D-CI-amidine, CI4-amidine, CAY10723, GSK484, EZP-6438, A-395, EED226, tubastatin, SIS3, centrinone B, or any combination thereof.

Aspect 33. The method of aspect 26, wherein one or more reactive oxygen species at the one or more sites of vascular damage cleaves the hydrophobic end group, wherein cleavage of the hydrophobic end group triggers release of one or more water soluble byproducts and a transition of the unimolecular nanoparticles to hydrophilic nanoparticles.

Aspect 34. The method of any one of aspects 26-33, wherein the subject is a human.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Figures 6A, 6B:
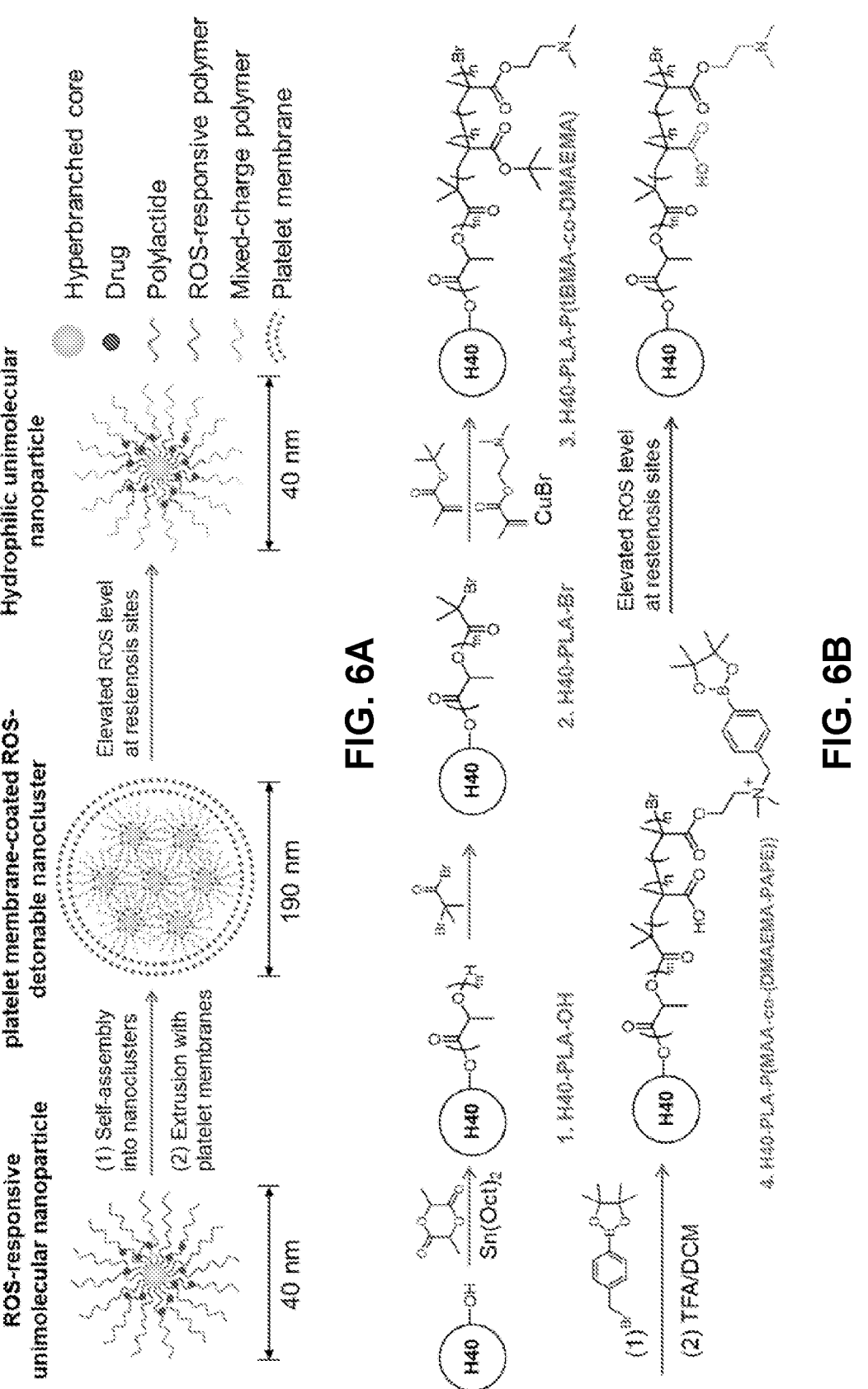
FIGS. 6A-6B show a schematic illustration for the synthesis of the unimolecular nanoparticles with ROS-detonable chemistry and the assembly of biomimetic nanoclusters.

Example 1: Design, Synthesis, and Characterization of the Platelet Membrane-Coated, ROS-Detonable Nanoclusters Herein, is disclosed a nanocluster that can enable multi-functionality ideal for anti-restenotic therapy. The nanocluster core was formed by self-assembly of unimolecular nanoparticles H40-polylactide-block-poly{methacrylic acid-ran-2-(methacryloyloxy)-N,N-dimethyl-N-[4-(4,4,5,5-tetramethyl-1,3,2-dioxaborolan-2-yl)benzyl]ethan-1-aminium} (H40-PLA-P(MAA-co-(DMAEMA-PAPE), FIGS. 6A-6B). H40-PLA-OH (Polymer 1 in FIGS. 6A-6B) was first synthesized by ring-opening polymerization of D,L-lactide monomer using hyperbranched polyester Boltorn® H40-OH as the macromolecular initiator. Then, H40-PLA-OH was reacted with 2-bromoisobutyryl bromide via esterification to yield 2-bromoisobutyryl terminated H40-polylactide (H40-PLA-Br, Polymer 2 in FIGS. 6A-6B). Thereafter, H40-polylactide-block-poly(tert-butyl methacrylate-ran-2-(dimethylamino)ethyl methacrylate (H40-PLA-P(tBMA-co-DMAEMA), Polymer 3 in FIGS. 6A-6B) was synthesized by ATRP using H40-PLA-Br as the bromide initiator. The hydrophobic phenylboronic ester was conjugated to the tertiary amine group to obtain H40-polylactide-block-poly{tert-butyl methacrylate-ran-2-(methacryloyloxy)-N,N-dimethyl-N-[4-(4,4,5,5-tetramethyl-1,3,2-dioxaborolan-2-yl)benzyl]ethan-1-aminium} (H40-PLA-P(tBMA-co-(DMAEMA-PAPE))). The final product used to prepare unimolecular nanoparticles (i.e., H40-PLA-P(MAA-co-(DMAEMA-PAPE)), Polymer 4 in FIGS. 6A-6B) were obtained after deprotection of tert-butyl alcohol. The structure of all intermediate and final products was verified by $^1$H NMR. The nanoclusters were self-assembled from multiple small unimolecular nanoparticles due to the increased hydrophobicity after phenylboronic ester modification. Platelet membrane was coated onto the surface of the nanoclusters via an extrusion process to render the nanoclusters with biomimicry, stability, and solubility (hence injectability). dynamic light scattering (DLS) measurements showed that the hydrodynamic diameter of the biomimetic nanoclusters was 192.5±2.1 nm, and the surface zeta potential was −29.7±1.0 mV. Notably, without platelet membrane coating, the unimolecular nanoparticles were not stable and can readily form aggregates in an aqueous solution via hydrophobic interaction. The loading efficiency and loading capacity of the RVX in the biomimetic nanoclusters quantified by reversed-phase high-performance liquid chromatography (HPLC) were 89% and 10.6%, respectively.

Figure 1B:
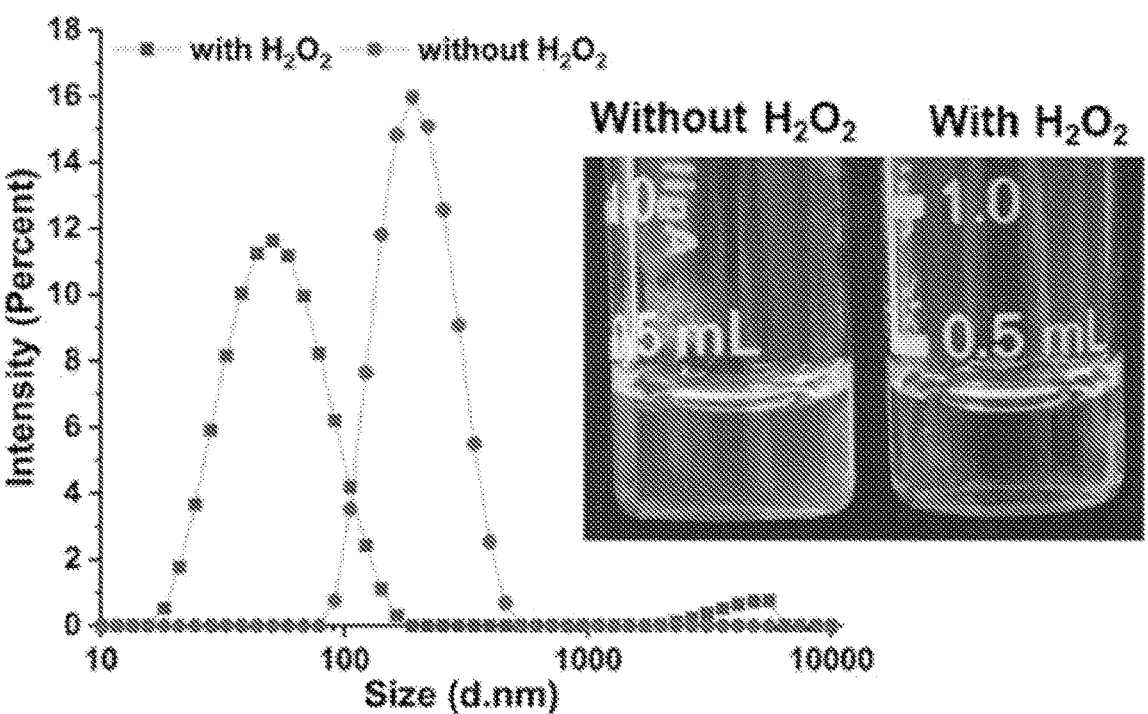
Figures 1C, 1D:
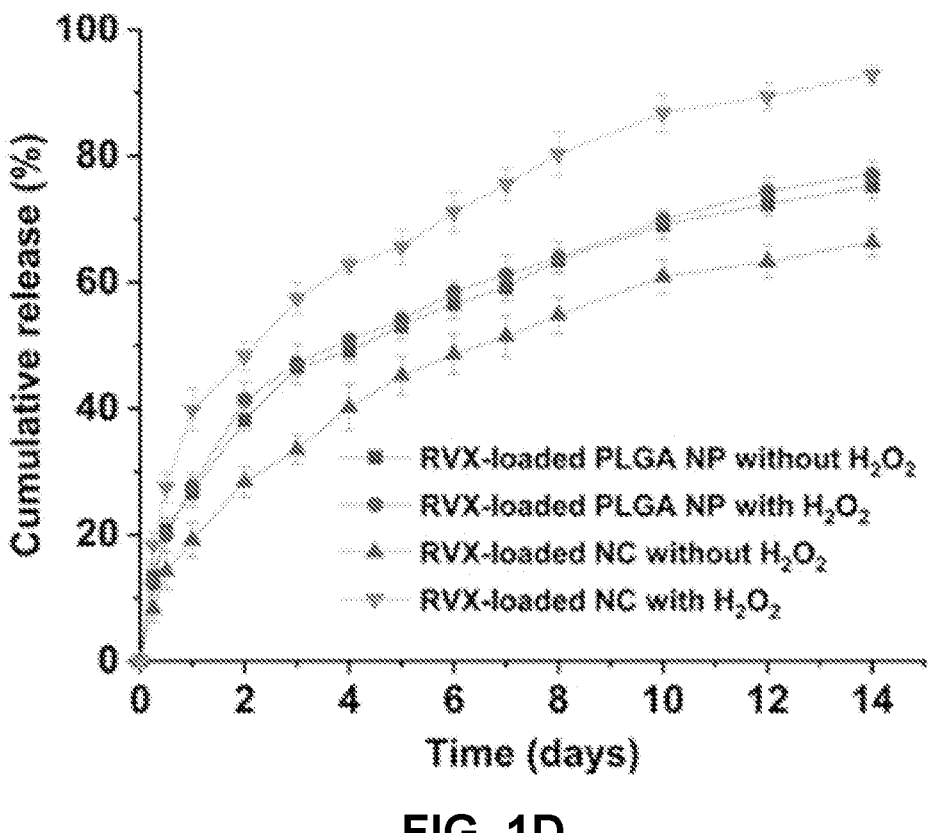

Excessive accumulation of ROS has been well documented in diseased vasculatures such as in the cases of atherosclerosis and angioplastied or stented vessels. Taking advantage of this pathophysiological feature, a ROS-detonable "trigger" was designed for the disclosed nanoclusters to enable "on-demand" size transition specifically at the lesion site (FIG. 1A). To showcase this feature, the biomimetic nanoclusters were transiently exposed to hydrogen peroxide ($H_2O_2$) at a physiologically relevant concentration as a surrogate of ROS. The changes of particle size and morphology were monitored by DLS and transmission electron microscope (TEM), respectively, in the presence of 100 μM $H_2O_2$. As presented in FIG. 1B, the size distribution dramatically changed in response to $H_2O_2$ as a characteristic peak appeared in around 40 nm, indicating that the biomimetic nanoclusters degraded into smaller nanoparticles. Moreover, turbidity of the nanoparticles solution remarkably changed from light blue opalescence to clear after the incubation with $H_2O_2$. TEM images showed the formation of the distinctive biomimetic nanoclusters and consistent membrane coatings over the nanocores. In addition, TEM visualization also confirmed the detonation of the biomimetic nanoclusters after $H_2O_2$ treatment (FIG. 1C). The biomimetic nanoclusters were penetrated by $H_2O_2$, which quickly oxidizes and cleaves off the hydrophobic phenylboronic ester, converts the hydrophobic nanoparticle to hydrophilic, and generates two types of water-soluble small molecules, i.e., 4-(hydroxymethyl)phenol and boronic acid. The drastically reduced hydrophobic interactions between small unimolecular nanoparticles resulting from the ROS-triggered hydrophobic to hydrophilic transition and the two water soluble byproducts led to an increased osmotic pressure within the platelet membrane-coated nanocluster and subsequently, the disassembly of the nanoclusters, thereby releasing the small-sized nanoparticles ideal for deep tissue penetration. Moreover, the influence of $H_2O_2$ on in vitro drug release profile of the nanoparticles was evaluated. The drug release behavior of the PLGA NP was not affected by $H_2O_2$, while an increased drug release was observed for the nanoclusters (NC) in the presence of $H_2O_2$, which further demonstrated the ROS responsiveness of the nanoclusters (FIG. 1D).

Figure 2A:
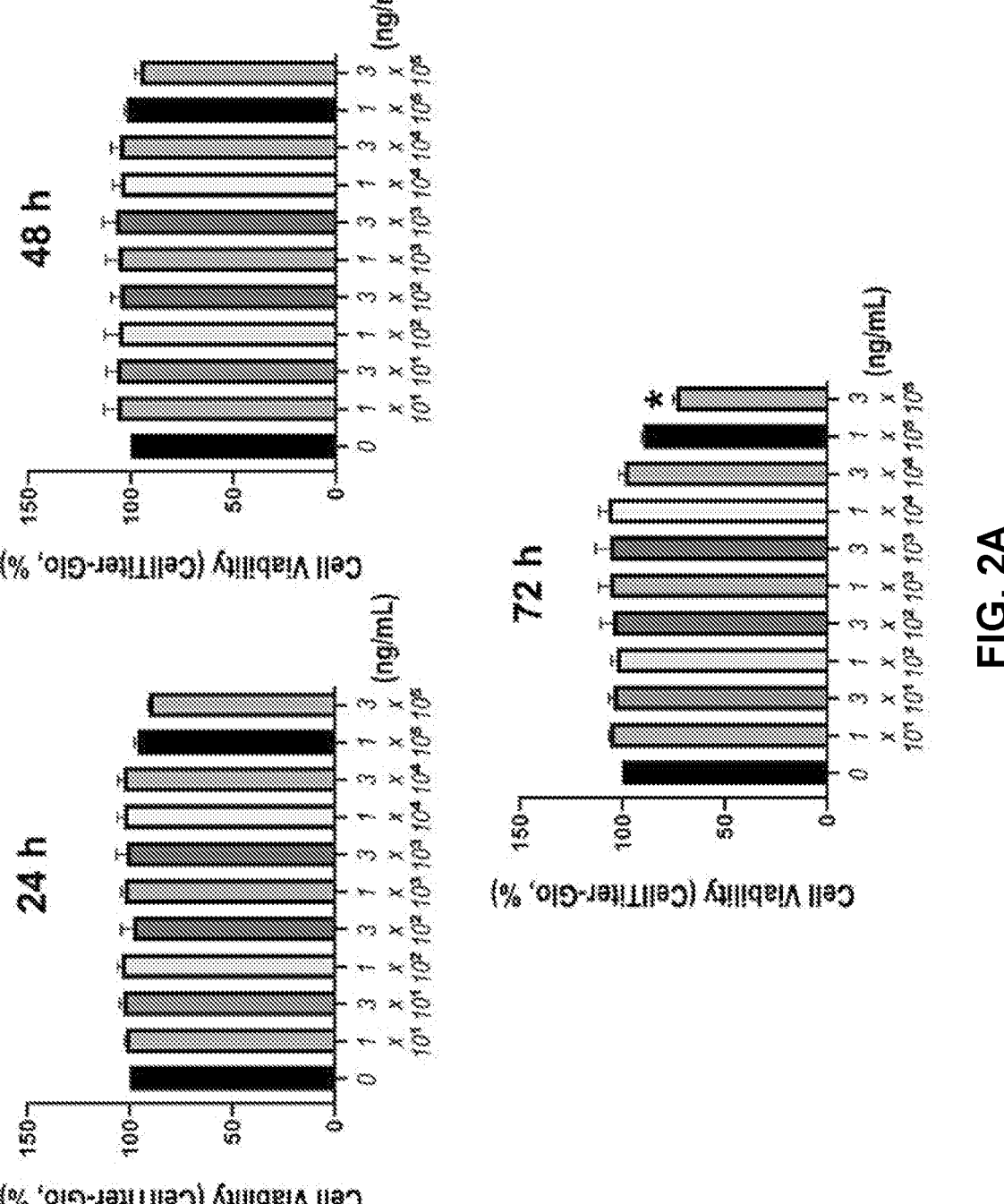
FIGS. 2A-2C show in vitro cytotoxicity and anti-proliferation activities of the platelet membrane-coated, ROS-detonable nanoclusters in VSMC.
Figure 2B:
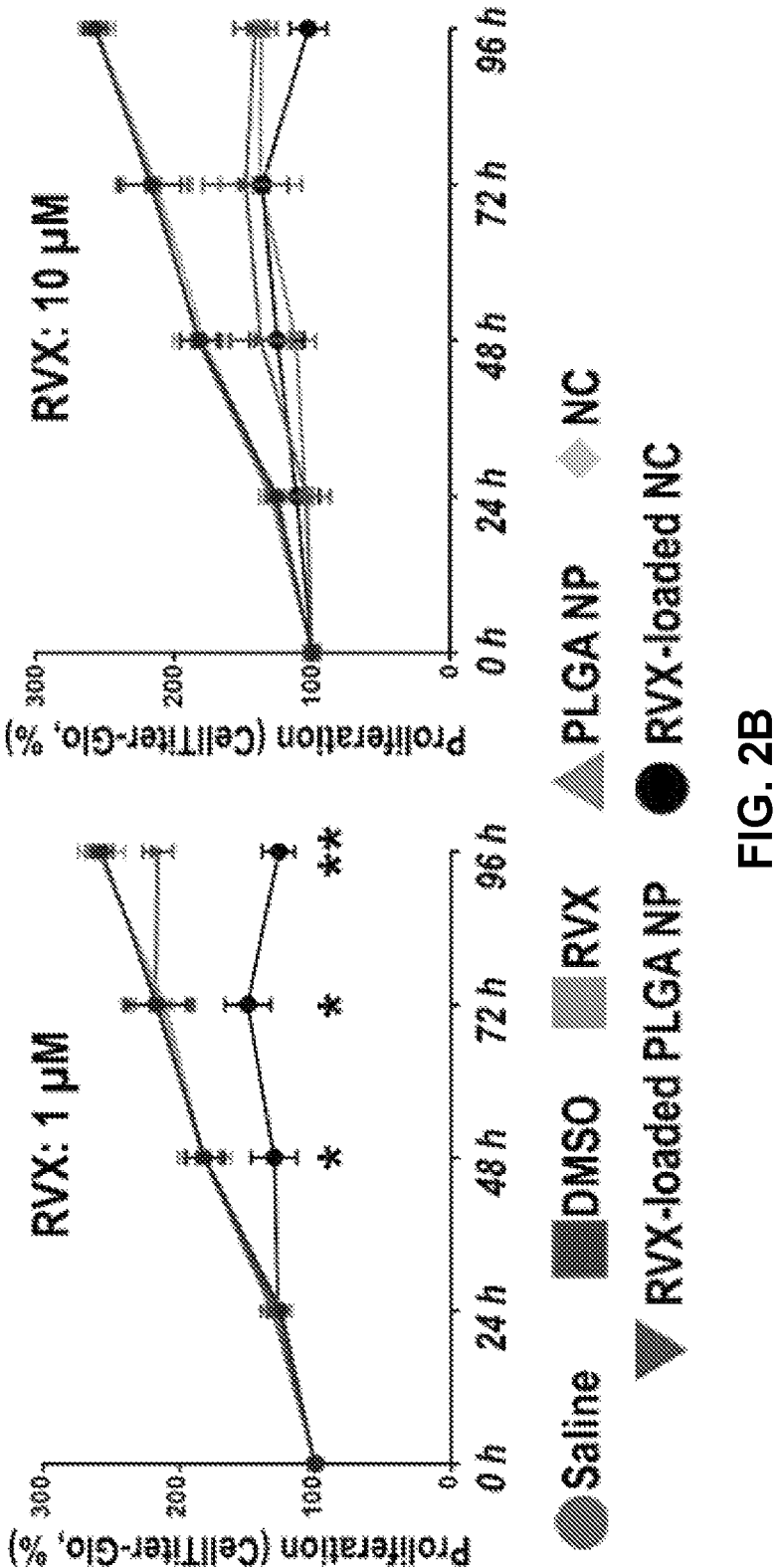

Example 2: The Multimodal Nanocluster Enables Efficient Delivery of Anti-Restenotic Payload In Vitro To evaluate the cytotoxicity of the nanoclusters via Cell-Titer-Glo Luminescent cell viability assay, VSMC were incubated with various concentrations (varied from 0 to 1 mg/mL) of NC for 24, 48, or 72 h. As presented in FIG. 2A, no obvious toxicity was observed at concentrations less than 300 μg/mL It is well known that the excessive proliferation of VSMC is the deciding factor behind the pathogenesis of IH and hence restenosis. After endovascular injuries (e.g., angioplasty or stenting), VSMC are exposed to a milieu highly enriched in cytokines, growth factors, and ROS; and consequently, in the present study, platelet-derived growth factor BB (PDGF-BB), one of the most prominent growth factors in restenotic environment, was utilized to induce VSMC proliferation and ROS induction, as established in prior studies. VSMC were then subjected to treatment with various formulations of RVX, an emerging anti-restenotic drug with a suboptimal pharmacological profile. These include RVX in free solution, or RVX-loaded NC, or RVX-loaded PLGA NP. Vehicle control groups were also included for comparison (e.g., saline, DMSO, and empty NC and PLGA NP). As shown in FIG. 2B, in the saline and DMSO treatment group, PDGF-BB robustly stimulated the proliferation of VSMC, whereas treatment with a low dose RVX (1 μM, either in its free solution or RVX-loaded PLGA NP formulation) failed to exert any notable effect. In contrast, incubation with RVX-loaded NC with the same RVX concentration effectively inhibited VSMC proliferation, with 35%, 40%, 52% reductions at 48 h, 72 h, and 96 h, respectively. Additionally, APOA-I, a vascular protective gene that can be specifically mobilized by RVX as shown in recent clinical trials, was upregulated exclusively in VSMC treated with the disclosed nanocluster formulation (RVX-loaded NC, FIG. 2C). This could be due to the improved intracellular drug release of RVX-loaded NC in response to PDGF-BB-induced intracellular ROS enrichment in VSMC. Of note, at a dosage of 10 μM as commonly used in vitro, all formulations of RVX unanimously led to effective inhibition of VSMC proliferation (FIG. 2B).

Figures 2C, 3A:
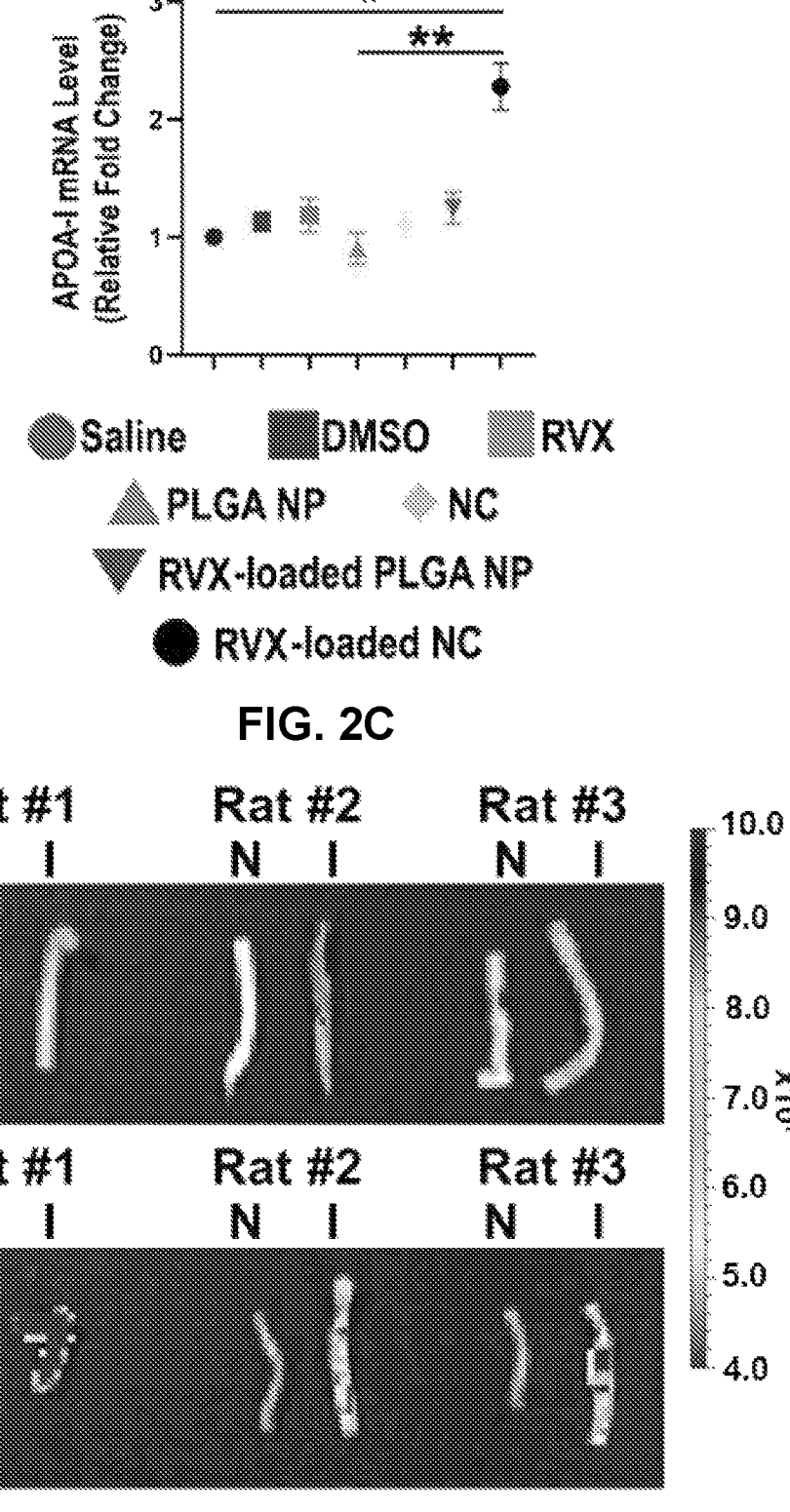
FIGS. 3A-3C show the platelet membrane-coated, ROS-detonable nanocluster enabled improved lesion-targeting capacity and biodistribution pattern.
Figure 3B:
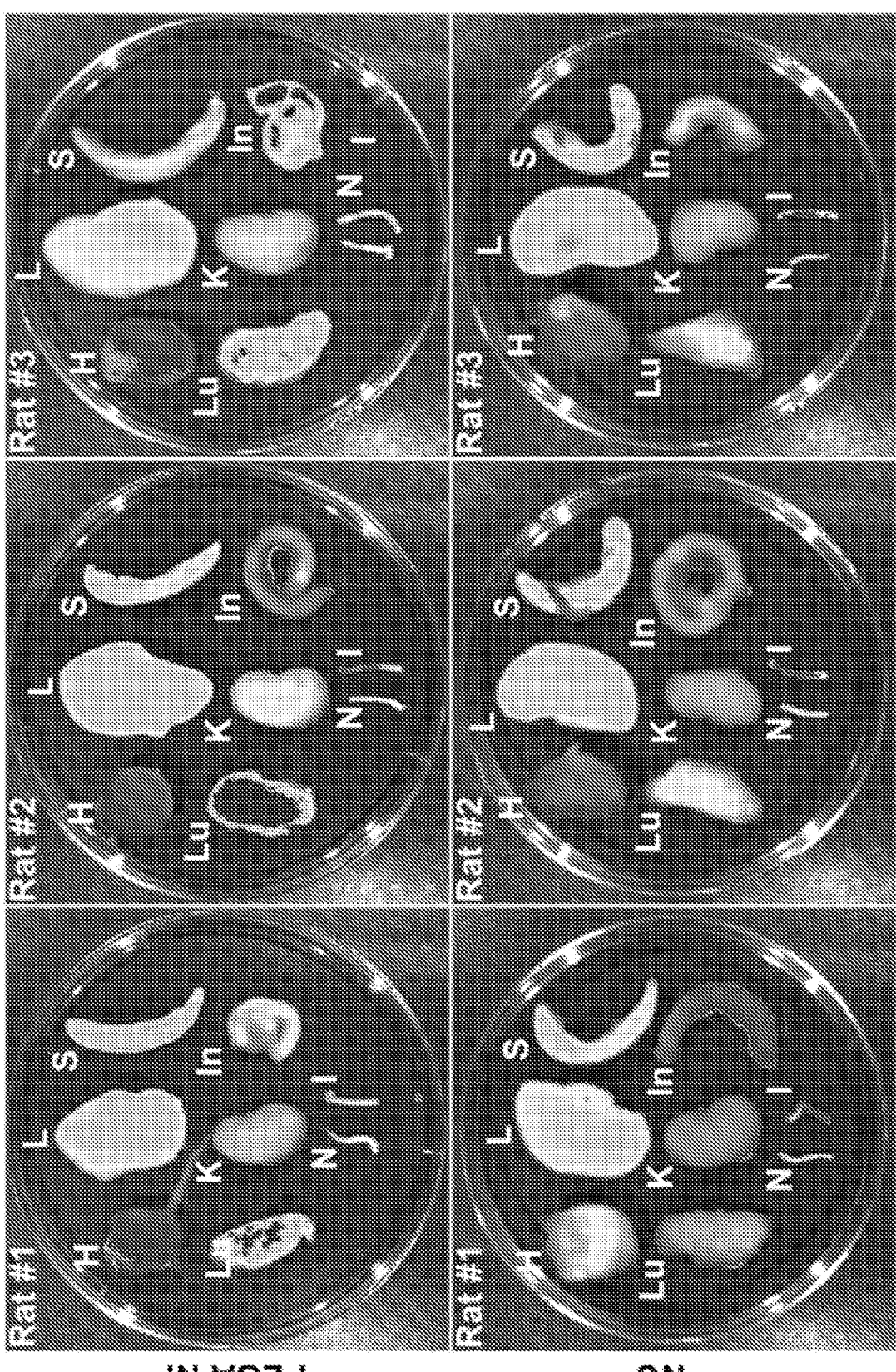
Figure 3C:
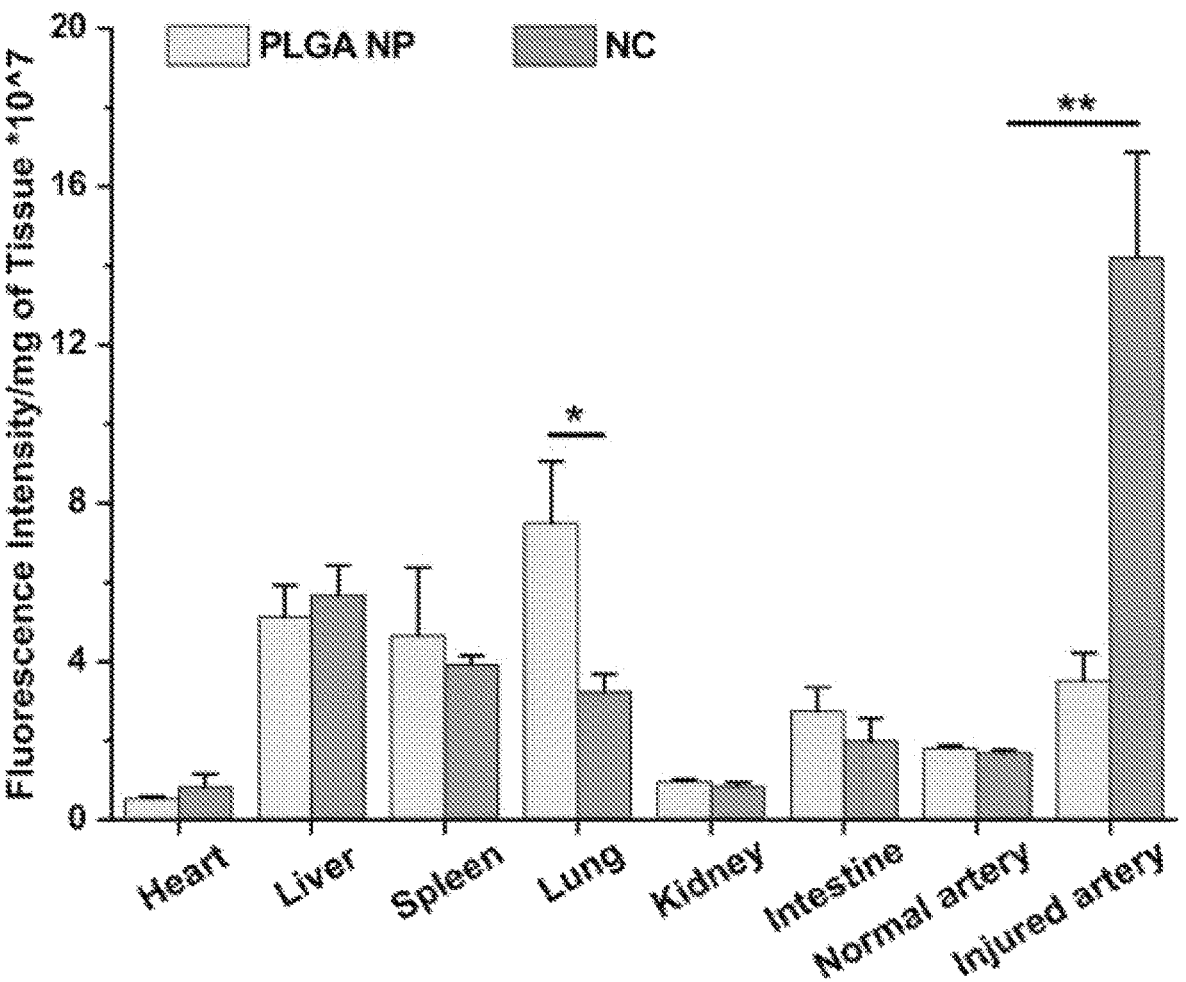

Example 3: The Platelet Membrane-Coated, ROS-Detonable Nanocluster Demonstrates Superior Targetability, Biodistribution, and Tissue Penetration In Vivo To determine the targeting specificity and whole-body biodistribution, a balloon angioplasty-induced carotid artery injury model was established in rats. Cy5.5-loaded NC or control PLGA NP of similar particle size were injected via tail vein immediately after balloon injury. 24 h later, the main organs and injured and non-injured carotid arteries were excised for ex vivo imaging (FIGS. 3A-3C). As demonstrated in FIG. 3A, the platelet membrane coating enabled highly enriched fluorescence signal in the injured carotid arteries over non-injured contralateral control for both nanoparticles, which is consistent with previous results. This active targeting ability is likely due to the specific interaction between glycoprotein VI on the platelet membrane with collagen exposed at the injury site. Moreover, the targeting specificity (shown as fluorescence signal ratio between injured and non-injured arteries in each rat) in the Cy5.5-loaded NC group was significantly higher than the Cy5.5-loaded PLGA NP group with an equivalent amount of Cy5.5. Additionally, PLGA NP displayed a suboptimal biodistribution profile with potential off-target issues, as evidenced by extensive accumulation in lung and liver (FIG. 3B). In contrast, the disclosed NC demonstrated significantly enhanced targeting specificity, with a 4-fold superior performance (injured-to-un-injured signal ratio) over PLGA NP (FIG. 3C). Moreover, significantly less (~50%) lung accumulation was noted in animals administered with NC versus PLGA NP group.

Figure 4:
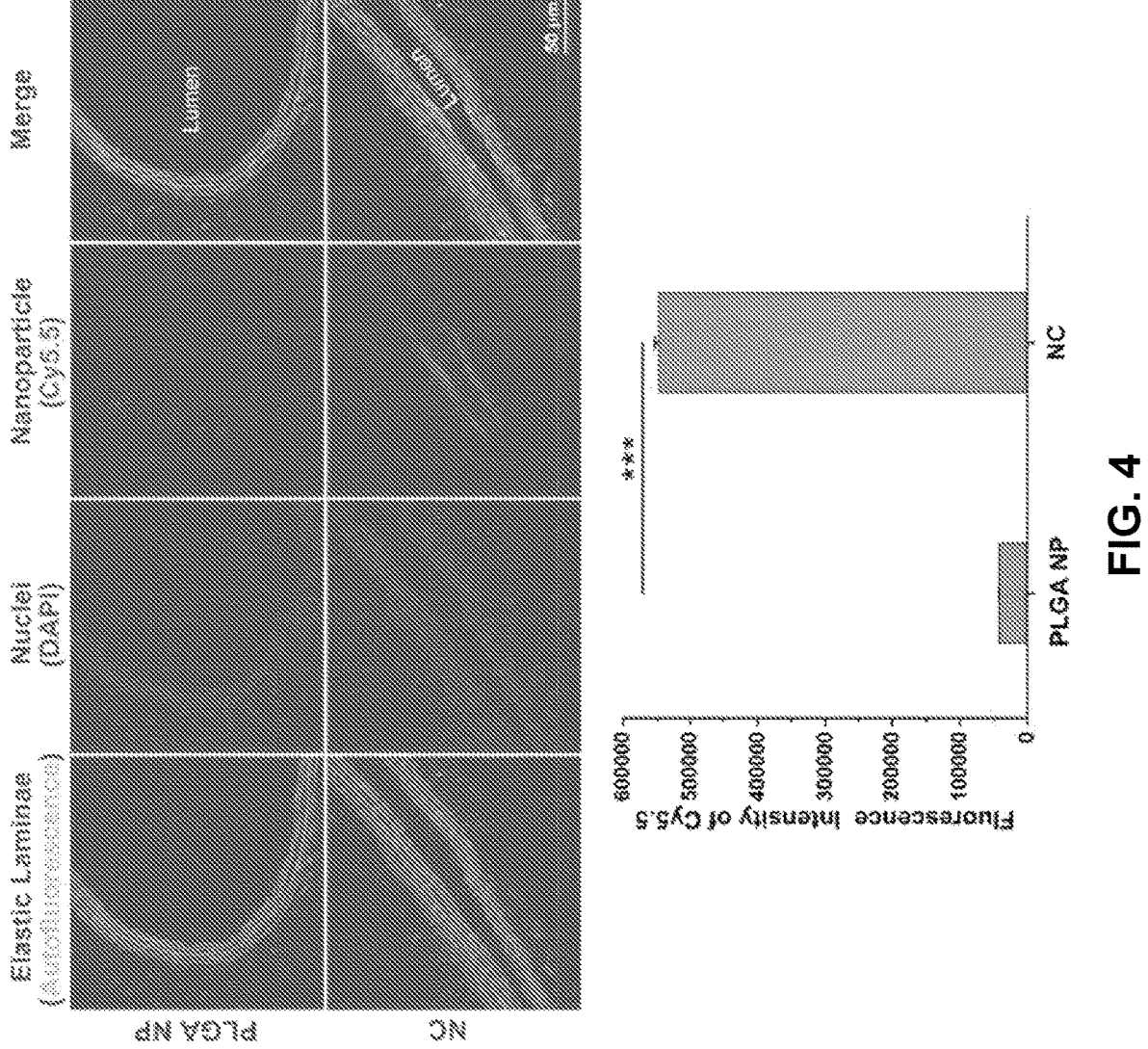
FIG. 4 shows fluorescence images of the injured carotid artery cross sections. Left column: the autofluorescence of the internal elastic lamina. Second column from left: 4',6-diamidino-2-phenylindole (DAPI) stained nuclei. Third column from left: Cy5.5 signal. Scale bar: 50 µm. Cy5.5-loaded PLGA NP and Cy5.5-loaded NC were administered systemically following vascular injury. 24 h later, the injured carotid arteries were collected and sliced. Slides were stained with DAPI for nuclei and visualized by confocal laser scanning microscopy. Quantitative analysis of the fluorescence intensity of Cy5.5 using Image J. Data are presented as mean±SEM (n=3). ***P<0.001 with Student's t-test.

To compare the tissue penetration capabilities of the two nanoparticles, the injured carotid arteries excised from rats treated with Cy5.5-loaded NC or PLGA NP via intravenous injections were studied using a confocal microscopy. As shown in FIG. 4, autofluorescence of the internal elastic lamina (left column), and cell nuclei were counterstained with DAPI as shown in the second column from the left. Cy5.5-loaded nanoaprticles' signal is shown in the third column from the left. Consistent with the findings from the IVIS study, arterial cross-sectional images from the PLGA NP-treated rats showed minimal Cy5.5 fluorescence signal, exclusively located in the near-luminal intimal layer. The presence of NC, on the other hand, was readily observable in the distal layers of the vessel wall, shown as fluorescent puncta in medial layer. Collectively, these data support a superior tissue penetrating capacity of the ROS-detonable nanocluster over the conventional nanoplatform.

Figure 5A:
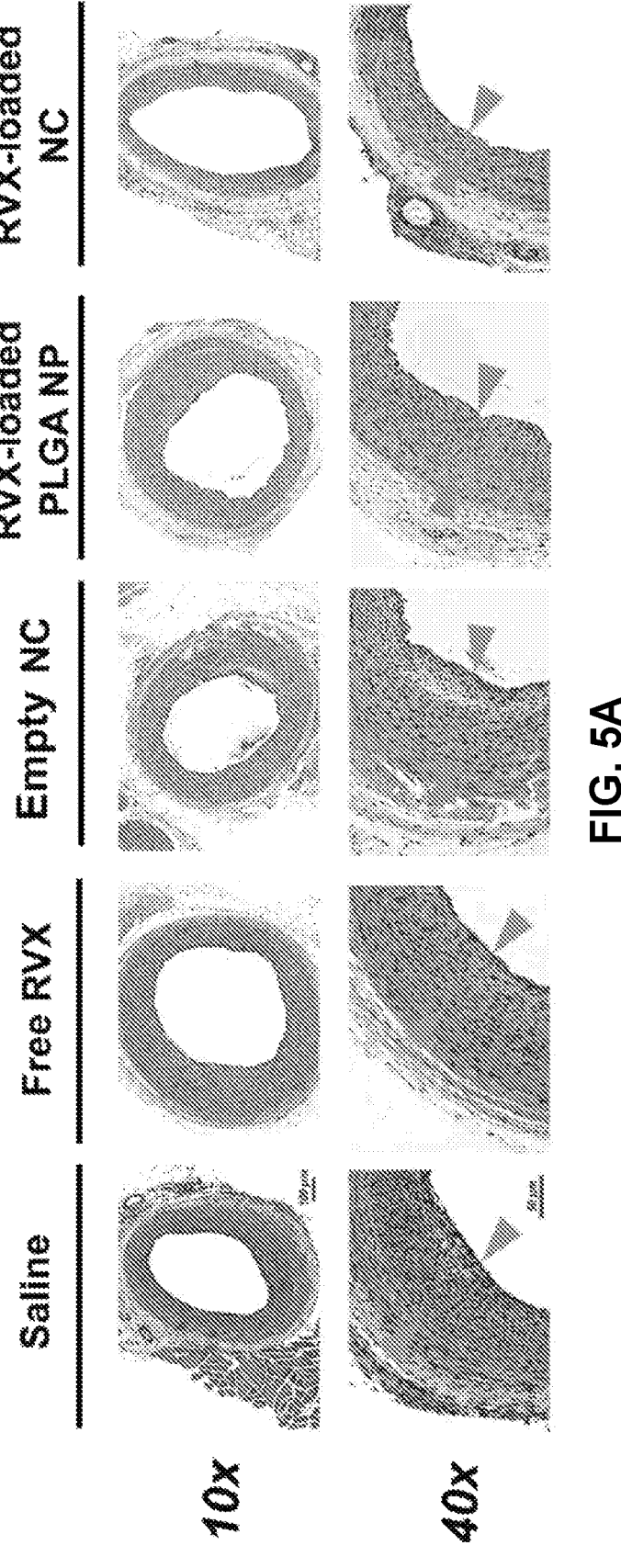
FIGS. 5A-5B show anti-restenotic effects of the biomimetic nanoclusters in a balloon angioplasty-induced carotid artery injury model.
Figure 5B:
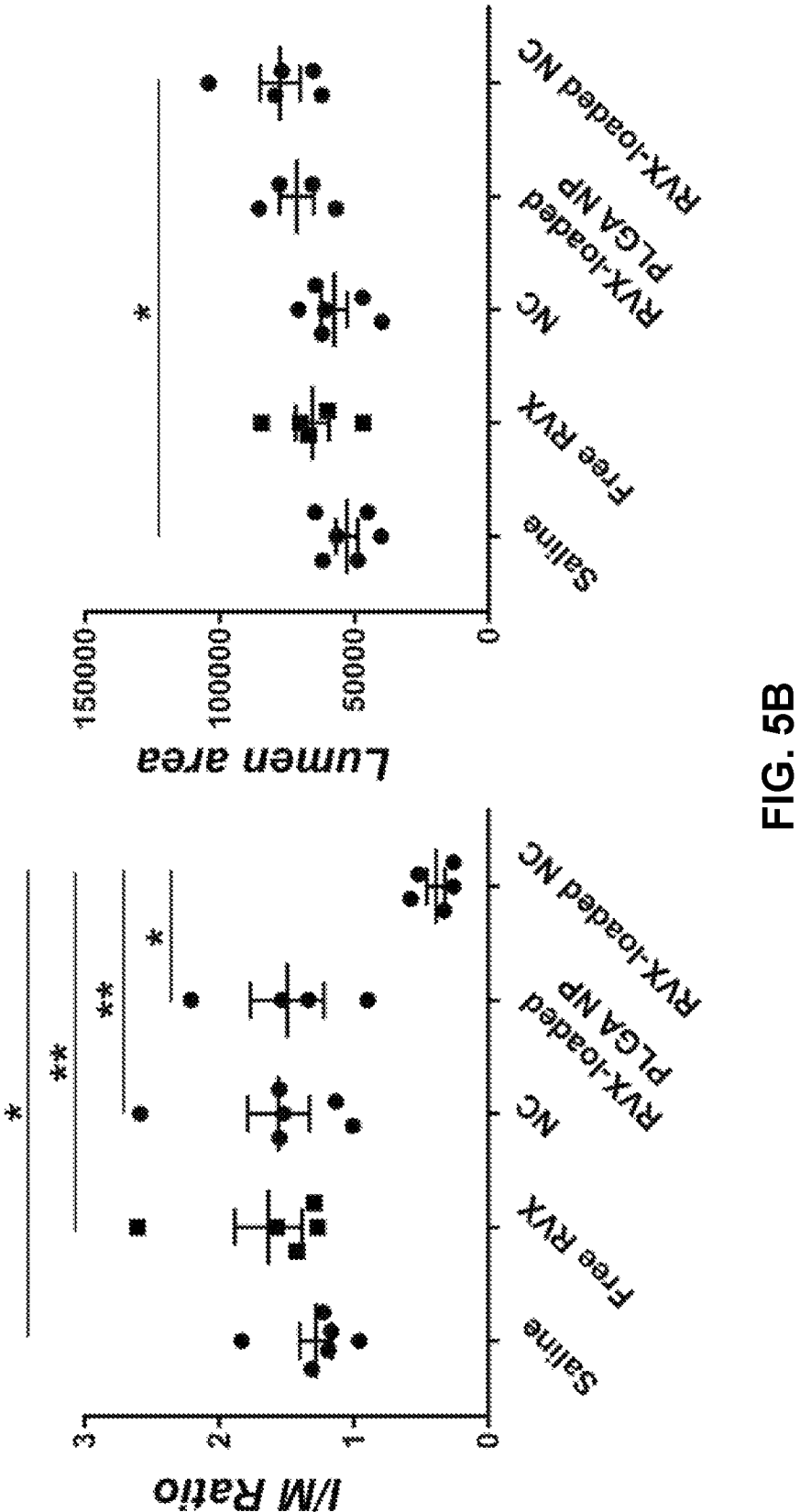

Example 4: RVX-Loaded ROS-Responsive Nanoclusters, but not Conventional RVX-Loaded PLGA NP, LED to Effective Amelioration of IH Prompted by the improved performances of the multi-modal nanocluster, the anti-restenotic potency of RVX delivered through NC was then determined in comparison to the RVX-loaded PLGA NP. Immediately following angioplasty, rats received one-time intravenous injection of the nano-formulated RVX (10 mg/kg) or control treatment (saline, DMSO vehicle, empty NC). Two weeks following angioplasty, rats were euthanized, and the carotid arteries were collected for morphometric analysis. I/M ratio and lumen area were quantified to evaluate the vascular remodeling efficacy. As shown in FIGS. 5A-5B, the empty NC did not exert any deleterious changes in the injured arteries, such as luminal restriction or immune cell infiltrations. Amongst the 3 formulations of RVX, only RVX-loaded NC elicited effective mitigation of IH. In contrast, neither free RVX solution nor that delivered through conventional PLGA NP led to any significant changes in intima-to-media (I/M) ratio. Moreover, a significant expansion of lumen area could be observed with treatment of RVX-loaded NC, but not other formulations of RVX. These evidence indicates that efficient delivery through the disclosed nanoplatform with preferred targetability and tissue penetration can significantly reduce the effective dose required for RVX, an emerging cardiovascular drug with an undesirable pharmacological profile. Additionally, no signs of systemic toxicity could be observed, as demonstrated by the normal histological features of heart, lung, kidney, spleen, and liver, as well as the minimal changes in gene transcription levels of inflammatory (TNFα and MCP1) and apoptotic markers (BAX and Caspase3) from spleen and liver tissue homogenates.

Example 5: Discussion and Conclusions

Current anti-restenotic methods, including DES (standard-of-care), are plagued with significant drawbacks. They still leave a significant portion of patients unprotected from restenosis, particularly those with obesity and diabetes or with peripheral artery diseases (e.g. lower extremities, up to 75% incidence). In fact, stenting and angioplasty may not be applicable or suboptimal to small-diameter extremity vessels. Moreover, serious safety concerns, including thrombosis and increased mortality have been recently reported as resulting from both DES and DCB.9 Additionally, once a DES or DCB is deployed, the anti-restenotic payload will be released within several weeks or days, therefore only affording a highly fixed regimen with no flexibility. Alternative stent-free strategies that could offer more effective yet safer targeted delivery of anti-restenotic agents will bring tremendous benefits to these patients.

The advent of nanotechnology ushers in a new era for targeted drug delivery. Currently, more than 60 nanomedicine have been approved by FDA or received the Conformité Européenne (CE) marking, mostly for cancer treatment. Unfortunately, there remains a paucity of clinically approved or actively tested candidates for cardiovascular nanomedicine. Numerous types of nanoparticle-based therapies have been developed for anti-restenotic treatment due to their outstanding drug-loading and controlled-release properties, yet very few have entered human clinical trials. So far, the most successful ones mainly utilize a nanoparticle albumin bound drug (Nab) strategy, such as Nab-Paclitaxel (ABI-007). ABI-007 once entered phase I/II clinical trial (SNAPIST-I) for peripheral arterial diseases, but was later terminated.44-45 LABR-312, a liposomal nanoproduct loaded with alendronate, recently showed inspiring result from Phase IIb trial, indicating early efficacy in diabetic patients who received angioplasty and DES. Nevertheless, it is important to note that LABR-312 is mainly tested as an ancillary treatment, rather than an alternative to DES. In sum, despite the well documented safety and the potential advantages offered by nanomedicine, there has yet been any formal clinical evaluation and utility for anti-restenotic therapies.

Numerous nanoparticle designs have been reported with promising efficacy in pre-clinical models in recent years. To achieve targeted delivery to vascular lesion sites, various strategies have been adopted, ranging from surface ligand conjugation (e.g., collagen- or integrin-targeting peptides), to utilizing the shape-effect (e.g., cylindrical versus spherical nanostructures). Biomimetic surface functionalization represents a novel and highly promising strategy in targeted nanomedicine. A series of biomimetic (biomembrane-coated) nanoplatforms for cardiovascular applications has recently been developed. Platelets are the natural "first responders" to intravascular injuries, enabled through their spontaneous homing and prompt accumulation to vascular lesion sites. Taking advantage of the plural targeting ligands endogenously expressed on the membrane surface of platelets, nanoparticles coated with platelet-derived membranes could display various biomimetic features, including the endovascular lesion-targeting capacity and certain level of biocompatibility. Additionally, due to the lack of intracellular contents essential to trigger the coagulation cascades, such platelet membrane coating strategies are free from concerns of increased thrombogenicity.

However, certain limitations exist in the earlier designs of nanoparticle-based therapies and biomimetic nanomedicine—most notably, the suboptimal tissue penetration and biodistribution. In the case of DES, these two issues were naturally solved by the physical presence of the drug-bearing devices deep inside the multi-layered vessel wall. Therefore, there remain major obstacles for nanoparticle-based therapies to overcome in order to outcompete the current standard-of-care. In the seminal work by Che-Ming J Hu et al. in which the biomimetic biointerfacing concept was first put into test, the presence of platelet membrane-coated conventional PLGA nanoparticles and its fluorescent payload (i.e., docetaxel) was primarily seen in the luminal layer of the vessel wall, with minimal penetration into the medial and adventitial layers. Moreover, despite the outstanding lesion selectivity between injured versus non-injured arteries and ultimately a promising therapeutic efficacy, a closer look at the biodistribution unveiled a liver/spleen-predominant pattern of retention over the arterial tissue, thereby posing a potential risk of significant "off-target" risk. This was similarly observed in a recent study with a prototypic design of platelet membrane-coated nanostructure for anti-restenotic application. Suffices to say that major innovation is needed to improve the tissue penetration capability and biodistribution of nanoparticle-based anti-restenotic therapies.

Size matters—there is no such thing as one-size-fits-all in nanoparticle applications in complex biology. It is increasingly recognized that nanoparticle size plays a vital role in its biodistribution and tissue/cell penetration. For longer circulation (less organ entrapment), a larger size is favorable, whereas a smaller size is desirable for better lesion penetration—it is impossible to have both in the same nanoparticle. To solve this dilemma, a size-tunable nanocluster was designed that could help attain optimal biodistribution and tissue penetration simultaneously. That is, a nanocluster (~190 nm) formed with small unimolecular nanoparticles circulates in the blood flow until it reaches the target restenotic lesion (guided through its platelet membrane coating). Once attached there, it is exposed to excessive ROS, which triggers the disclosed innovative ROS-responsive detonation chemistry. The small molecule byproducts from this cleavage reaction (i.e., 4-(hydroxymethyl)phenol and boronic acid) together with the resulting hydrophilic nanoparticles then generate an osmotic pressure, which swells and bursts the membrane coating, and the small hydrophilic nanoparticles are released to penetrate through the multi-layered arterial wall into the restenotic lesion and provide sustained drug delivery.

Last but not least, the current study establishes the early pre-clinical evidence supporting the translational potential of the disclosed nanoplatform capable of significantly improving the performance of RVX, also known as Apabetalone. Targeting the second bromodomain of the BET protein family, RVX has demonstrated safety and early efficacy in clinical trials for management of diseases ranging from coronary and pulmonary artery diseases to metabolic syndrome (e.g., diabetes). Similar to its first-in-class inhibitor JQ1, RVX has a relatively short half-life (1.5 hours) and therefore typically requires a twice-daily (b.i.d) regimen. In rodent studies, the reported dosages can reach 150 mg/kg/day in cardiovascular disease models. Therefore, the disclosed technology presents a major improvement of an RVX-based anti-restenotic therapy (10 mg/kg, once over 2-week window) over the conventional formulations (50-150 mg/kg/day)—not only that it could enhance the drug efficacy through the targeted delivery, but the much less frequent dosing could also address the patient non-adherence issue persistently observed in b.i.d regimens. Other promising anti-restenotic drugs with established toxicities or suboptimal biodistribution, such as paclitaxel and dexamethasone may broadly benefit from the disclosed nanoplatform, although further validations are warranted.

Restenosis is the main culprit behind the high failure rate of endovascular interventions. The mainstream anti-restenotic solutions, such as DES and DCB, are plagued with grave safety concerns. In search of an alternative strategy that can potentially replace DES, a highly innovative nanostructure was developed that was judiciously designed for stent-free applications in cardiovascular diseases. This multimodal nanocluster possess several key features that are most preferred for anti-restenotic therapy, including targetability (through platelet membrane coating), deep tissue penetration and optimal biodistribution (through an ROS-detonable size transition), and ROS-responsive drug release (through the H40-PLA-based unimolecular nanoparticle). Overall, the rationally engineered platelet membrane-coated, ROS-detonable nanocluster could provide new insight into the optimal design of multifunctional nanomedicine specifically catered for non-invasive management of cardiovascular diseases.

Example 6: Materials and Methods

Materials. Boltorn® H40 (a hyperbranched polyester with 64 hydroxyl terminal groups, molecular weight ~7.3 kDa) was kindly provided by Perstorp Polyols Inc., USA, and purified by fractional precipitation in acetone and tetrahydrofuran (THF). Tin(II) 2-ethylhexanoate ($Sn(Oct)_2$), triethylamine, tert-Butyl methacrylate, 2-(dimethylamino)ethyl methacrylate, copper(I) bromide (CuBr), and trifluoroacetic acid (TFA) were purchased from Sigma-Aldrich (St. Louis, MO, USA), respectively. D,L-lactide, pentamethyldiethylenetriamine, and 2-(4-(bromomethyl)phenyl)-4,4,5,5-tetramethyl-1,3,2-dioxaborolane were purchased from TCI (Tokyo, Japan), respectively. 2-bromoisobutyryl bromide and neutral aluminum oxide ($Al_2O_3$) for chromatography were purchased from Acros Organics (Pittsburgh, PA, USA). RVX-208 was purchased from ApexBio (Houston, TX).

Poly(lactic-co-glycolic acid) (PLGA) was obtained from LACTEL Absorbable Polymers (Birmingham, AL USA). Other reagents were purchased from ThermoFisher Scientific (Fitchburg, WI, USA) and used as received unless otherwise stated.

Platelet Membrane Derivation. Platelet-derived membrane was generated using a freeze-thaw process. Aliquots of platelet suspensions were frozen at −80° C., thawed, and pelleted by centrifugation. Pellets were washed with phosphate buffered saline (PBS) mixed with protease inhibitor. In some cases, the process was repeated one or more additional times. Pelleted platelet membranes were suspended in water and sonicated. Platelet membrane vesicle size was measured using dynamic light scattering and vesicles were morphologically examined using transmission electron microscopy. Membranes derived from other cell types are prepared in an analogous manner (e.g. performing repeated freeze-thaw cycles of other isolated cell types including macrophages, leukocytes, and the like).

Membrane coating of polymeric cores is accomplished by sonication of isolated membranes with the polymeric cores. Since morphological characteristics of polymeric cores have been determined, surface area—and thus needed membrane surface area—can be calculated, and volume of membrane stock solution to be added is determined based on concentration of the stock solution and required surface area.

Membranes derived from blood cells can be derived from O⁻ blood cells in order to avoid eliciting an immune response during treatment.

Cell Culture. Human aortic VSMC and culture media (SmBm-2 basal medium for experimental purposes, and SmGm-2 complete medium for expansion) were purchased from Lonza (Walkersville, MD). Cells between passages 5 and 7 were maintained at 37° C. with 5% $CO_2$ and used for all experiments. As established in previous studies, Accutase (ThermoFisher Scientific, Waltham, MA) instead of Trypsin was used for cell detachment to ensure fast cell adhesion and optimal cell status.

Synthesis of H40-PLA-OH. H40-PLA-OH was synthesized by ring-opening polymerization of the D,L-lactide monomer using dendrimer H40-OH as the macromolecular initiator. A 25 mL Schlenk flask was charged with H40-OH (200 mg), D,L-lactide (5 g), and $Sn(Oct)_2$ (35 mg). The reaction was carried out at 120° C. for 24 h. Thereafter, the mixture was cooled down to room temperature and dissolved in 5 mL of tetrahydrofuran (THF). The solution was added dropwise into methanol to yield a white precipitate. The precipitation process was repeated for 3 times and the final product was dried under vacuum overnight. The chemical structure was identified with a 400 MHz proton nuclear magnetic resonance ($^1$H NMR) spectrometer. 1H-NMR (400 MHz, CDCl₃, ppm): 5.2 (20H), 4.1-4.5 (2.61H), 1.6 (63H).

Synthesis of H40-PLA-Br. In a two-neck flask equipped with a magnetic stirrer, H40-PLA-OH (2 g) was dissolved in 60 mL of anhydrous THF and cooled to 0° C. in an ice bath. Then, triethylamine (2.19 mL) was added under nitrogen. 1.86 mL of 2-bromoisobutyryl bromide dissolved in 40 mL of anhydrous THF was added dropwise into the above solution at 0° C. The reaction was stirred at room temperature for 24 h. The solvent was removed by rotary evaporation and the product was purified by repeated precipitation in methanol and diethyl ether sequentially. The precipitate was collected and dried under vacuum to obtain a white product. $^1$H-NMR (400 MHz, CDCl₃, ppm): 5.2 (20.5H), 4.1-4.5 (2.1H), 2.0 (3.1H), 1.6 (63H).

Synthesis of H40-PLA-P(tBMA-co-DMAEMA). The H40-PLA-P(tBMA-co-DMAEMA) was synthesized by atom transfer radical polymerization (ATRP). In a typical polymerization procedure, H40-PLA-Br (200 mg), as a macromolecular initiator for ATRP, was dissolved in 2 mL of anhydrous THF in a 25 mL Schlenk flask (dried under vacuum prior to use) sealed with a rubber septum for degassing and kept under nitrogen. Tert-Butyl methacrylate (1.9 g), 2-(dimethylamino)ethyl methacrylate (1.7 g), and pentamethyldiethylenetriamine (PMDETA, 46.2 μL) was dissolved in 7 mL of anhydrous THF and placed in another 25 mL Schlenk flask, to which CuBr (31.8 mg) was added. The two flasks were degassed by freeze-pump-thaw cycles for three times. Then, the CuBr containing solution was added to the H40-PLA-Br solution via a syringe followed by three cycles of freezing-pumping-backfilling with nitrogen. The flask was then immersed in an oil bath set at 70° C. overnight. The polymerization was terminated by exposing the reaction mixture to air. Thereafter, the mixture was diluted by THF and passed through a neutral $Al_2O_3$ column to remove the residual copper catalyst. Then, THF was removed by rotary evaporation and the mixture was dissolved in chloroform. The solution was washed with brine for 3 times and dried with anhydrous $MgSO_4$ followed by filtration. The filtrate was evaporated by rotary evaporation. After repeated purification by dissolving in methanol and precipitating in deionized water for 4 times, a white product was obtained after drying under vacuum. $^1$H-NMR (400 MHz, CDCl₃, ppm): 5.2 (20.5H), 4.1 (117H), 2.6 (110H), 2.3 (330H), 1.7-2.1 (246H), 1.6 (59.9H), 1.4 (602H), 0.8-1.2 (373H).

Synthesis of H40-PLA-P(tBMA-co-(DMAEMA-PAPE)). H40-PLA-P(tBMA-co-DMAEMA) (313.4 mg) and 2-(4-(bromomethyl)phenyl)-4,4,5,5-tetramethyl-1,3,2-dioxaborolane (240 mg) were dissolved in 4 mL of chloroform under nitrogen in a 25 mL flask and reacted at 40° C. overnight. After concentration by rotary evaporation, the product was purified by repeated precipitation in diethyl ether. Then, the precipitate was collected and dried under vacuum. $^1$H-NMR (400 MHz, CDCl₃, ppm): 7.6-8.0 (3H), 4.9-5.4 (1.65H), 4.0-4.8 (2H), 2.7-3.8 (4.7H), 1.7-2.1 (3.9H), 1.2-1.5 (19.7H), 0.8-1.2 (7.9H).

Synthesis of H40-PLA-P(MAA-co-(DMAEMA-PAPE)). H40-PLA-P(tBMA-co-(DMAEMA-PAPE)) (500 mg) was dissolved in 3 mL of dichloromethane (DCM) and cooled to 0° C. in an ice bath. 3 mL of trifluoroacetic acid (TFA) was added dropwise into the above solution. After stirring at room temperature for 4 h, the mixture was dried by rotary evaporation, washed by diethyl ether, and dissolved in methanol. The product was then purified by dialysis (molecular weight cut off, 3.5 kDa) against deionized water to completely remove the free TFA. The final product was obtained by lyophilization. $^1$H-NMR (400 MHz, MeOD, ppm): 7.6-8.0 (3H), 5.2 (0.34H), 4.5-4.8 (2.3H), 4.0 (2H), 3.2 (4.6H), 1.7-2.5 (3.4H), 1.6 (1H) 1.4 (7.5H), 0.9-1.3 (7.9H).

Preparation of the RVX-Loaded Platelet Membrane-Coated Nanoclusters. H40-PLA-P(MAA-co-(DMAEMA-PAPE)) (3 mg) and RVX (1 mg) were dissolved in 200 μL of methanol and then added dropwise into the deionized water under sonication. Methanol was evaporated at 37° C. under reduced pressure. The RVX-loaded nanoclusters were obtained after lyophilization. The platelet membrane vesicles were derived as previously reported. Biomimetic nanoclusters were prepared by coating platelet membrane on the surface of the nanoclusters via the extrusion method. Briefly, platelet membrane vesicles were mixed with the pre-sonicated RVX-loaded nanoclusters at a membrane protein to polymer weight ratio of 1:1 and then extruded through a 400 nm and a 200 nm polycarbonate porous membrane sequentially using an Avanti mini extruder. The empty biomimetic nanoclusters were prepared following a similar procedure by extruding empty nanoclusters with the platelet membrane vesicles. Cy5.5-loaded biomimetic nano-clusters were prepared in the same way. RVX-loaded PLGA NP were prepared by fusing platelet membrane vesicles with PLGA nanocores that fabricated by a previously described nanoprecipitation method.57-58 RVX was mixed with PLGA in acetone and added dropwise into 0.05% poloxamer 188 containing aqueous solution. The solvent was evaporated by rotary evaporation.

Characterization of the Platelet Membrane-Coated, ROS-Detonable Nanoclusters. The hydrodynamic diameter and zeta potential of the biomimetic nanoclusters were obtained by DLS measurements by a ZetaSizer Nano ZS90 spectrometer (Malvern Instruments, USA) at a concentration of 0.1 mg/mL. The morphology of the biomimetic nanoclusters was characterized by TEM (FEI Tecnai G2 F30 TWIN 300 KV, E.A. Fischione Instruments, Inc. USA). Phosphotungstic acid solution (1%, w/w) was applied for the negative staining of the samples. Detonation of the biomimetic nanoclusters triggered by $H_2O_2$ was studied by incubation with 100 μM $H_2O_2$. The change of particle size and morphology of the biomimetic nanoclusters were monitored by DLS and TEM, respectively. Moreover, the digital photos were taken for direct illustration.

An ultrafiltration method was used to separate the unencapsulated drug from the biomimetic nanoclusters for the evaluation of the drug loading efficiency and loading capacity. Briefly, the biomimetic nanoclusters were added into the centrifugal filters (Millipore) with a molecular weight cutoff at 10 kDa, followed by centrifugation at 3000 rpm for 20 min. The amount of drug in the filtrate was measured by HPLC equipped with UV detection under 254 nm. Loading efficiency and loading capacity in percentages were calculated according to the following equations: loading efficiency (%)=(1−amount of unencapsulated drug/total amount of drug added)×100%. Loading capacity (%)=total weight of encapsulated drug/total weight of nanoparticles×100%.

In vitro release profiles of RVX from the biomimetic nanoclusters were studied by a dialysis method. Briefly, 1.5 mL of the biomimetic nanoclusters (1 mg/mL of RVX) was sealed in a cellulose membrane dialysis bag with a molecular weight cutoff at 3.5 kDa. Then, the bag was placed in 50 mL of PBS (0.1 M, pH 7.4) with or without 100 μM $H_2O_2$, which was then kept in a shaker (100 rpm) at 37° C. At certain time points, 0.2 mL of the release medium was collected to measure the amount of released RVX by HPLC at a wavelength of 254 nm. To maintain a constant medium volume, equivalent volumes of pre-warmed fresh medium were added back to the release medium after each sampling. The cumulative release amounts of RVX were calculated based on the standard curve.

Cell Viability Assay of the Nanoclusters. The cytotoxicity and anti-proliferation of the nanoclusters on VSMC was evaluated by a CellTiter-Glo Luminescent Cell Viability kit according to manufacturer's instructions. VSMC were cultured in 96-well plates (2×104 and 8×104 cells/well for experiments of proliferation and cytotoxicity, respectively) and grown for overnight. For cytotoxicity study, fresh basal medium (supplemented with 0.5% fetal bovine serum) containing NC with different concentrations were added into the plates. For proliferation study, VSMC were treated with 20 nM PDGF-BB to stimulate ROS and proliferation. Different formulations of RVX (free solution, RVX-loaded PLGA NP, or RVX-loaded NC) and vehicle controls at 1 μM or 10 μM were applied to the VSMC. VSMC treated with fresh medium alone were served as a control group. At each different time point (24 h, 48 h, 72 h, 96 h), 50 μL CellTiter-Glo reagent/50 μL PBS were added into each well upon removing the culture medium. Following 10 min incubation at room temperature, the 96-well plates were analyzed in a FlexStation 3 Benchtop Multi-Mode Microplate Reader (Molecular Devices, San Jose, California) (250-ms integration).

Rat Carotid Artery Balloon Angioplasty Model. All animal experiments conform to the protocols approved by the Animal Care and Use Committee (ACUC) of the University of Virginia. All adult male Sprague-Dawley rats (Charles River, weighing 300-350 g) were maintained in a temperature and humidity-controlled SPF level animal facility under a 12 h light-dark cycle. Food and water were available ad libitum. Animals were randomly assigned to each treatment group. The carotid artery balloon injury model was operated as previously described. In brief, after anesthesia with isoflurane (5% for inducing and 2% for maintaining), a mid-line incision in the neck was made, and the carotid arteries and carotid bifurcation were exposed by blunt dissection. The proximal of left carotid artery, inner carotid artery, and external carotid artery were then temporarily ligated with 5-0 nylon suture to avoid excessive blood loss during the surgery. A 1 mm arteriotomy was created on the distal segment of the external carotid arteries. Subsequently, a 2-French arterial balloon catheter (Edwards Scientific, Irvine, CA) was introduced through the arteriotomy and advanced ~1.5 cm into the common carotid arteries. The balloon catheter was slowly inflated at 1.5 atmosphere pressure followed by withdrawn to the carotid bifurcation for three times continuously with rotation to ensure complete denudation of the endothelium. The ligatures on the common carotid arteries were briefly lifted to check the status of back-bleeding (lack of back-bleeding indicates potential occlusion, and the animals will be excluded from the study). The external carotid arteries were then permanently ligated, and wounds were closed bioabsorbable sutures. Heating pad was provided as heat source during operation and the recovery phase. Analgesics and postoperative care were provided per ACUC policy.

Homing of the Biomimetic Nanoclusters to Injured Carotid Arteries. Following angioplasty-induced arterial denudation, the Cy5.5-loaded NC were intravenously injected via the tail vein. 24 h later, the animals were euthanized by $CO_2$ inhalation, and the main organs or tissues including heart, liver, spleen, lung, kidney, intestine, and the balloon-injured and non-injured carotid arteries were carefully collected for ex vivo fluorescence imaging by an in vivo imaging system (IVIS) with fluorescence excitation/emission wavelengths of 676/705 nm. The Cy5.5-loaded PLGA NP with similar particle size was used for comparation.

Tissue Penetration of the Biomimetic Nanoclusters into Medial Smooth Muscle Layer. To monitor the penetration of the biomimetic nanoclusters into the medial smooth muscle layer, the carotid arteries that harvested for ex vivo imaging were frozen in optimal cutting temperature (OCT) compound (VWR International) and then cut into 8 μm sections using a Cyrotome cryostat machine (Leica). The tissue sections were placed on polylysine-treated glass slides. Subsequently, the sections on slides were first washed with PBS to remove residual OCT compound and then incubated with DAPI for 15 min in a light-protected humidified chamber to stain nuclei. Then, the stained carotid artery cross sections were observed using a confocal laser scanning microscopy (CLSM, Nikon, Japan).

Morphometric Analysis of IH and Restenosis. Sprague-Dawley rats after carotid artery balloon injury were randomly assigned into 5 groups, including saline, free RVX, empty NC, RVX-loaded PLGA NP, and RVX-loaded NC group. The dose of RVX in all drug-containing groups was constant at 10 mg/kg. RVX-loaded biomimetic nanoparticles or compound solutions were immediately intravenously administrated after balloon injury. 2 weeks later, the animals were euthanized and fixed via transcardial perfusion of saline at a pressure of 100 mm Hg. The balloon-injured carotid arteries and relevant organs (e.g., heart, kidney, liver, spleen) were then carefully excised from the surrounding tissue. The collected specimens were sliced, with the majority portion of each for formalin-fixed, paraffin-embedded (FFPE) processing, and the rest for RNA extraction. Paraffin sections (5 μm per section) were obtained from the harvested arteries at equally spaced intervals. Haemotoxylin and Eosin (H&E) staining was performed for histopathological analysis. Area inside external elastic lamina (EEL area), area inside internal elastic lamina (IEL area), lumen area, intima area (=IEL area—lumen area), and media area (=EEL area—IEL area) were calculated using Image J. Intimal hyperplasia was defined as the ratio of intima area versus media area (Intima-to-media ratio, I/M ratio).

Biocompatibility-Histological Examination. After euthanasia, the main organs or tissues including heart, liver, spleen, and kidney were collected, fixed with 4% paraformaldehyde, and embedded in paraffin in a tissue base mold. The blocks were sectioned at a microtome setting of 5 μm for H&E staining The images were captured by an optical microscope for morphometric analysis.

Real-time Quantitative PCR (qRT-PCR) Analysis of mRNA Expression Levels in Cell Culture and Tissue Homoqenate. mRNA was isolated from cultured VSMC and collected carotid segments using TRIzol following the manufacturer's instructions. Purified mRNA (1 μg) was used for the first-strand cDNA synthesis and quantitative RT-PCR was performed using the QuantStudio3 (Applied Biosystems, Carlsbad, CA). Each cDNA template was amplified in triplicates using SYBR Green PCR Master Mix, with the following primer sets: Human APOA-I forward primer ACTGTGTACGTGGATGTGCTCAAAG (SEQ ID NO. 1), reverse primer CACGCTGTCCCAGTTGTCAAG (SEQ ID NO. 2); Human GAPDH forward primer ATTCCACC-CATGGCAAATTCC (SEQ ID NO. 3), reverse primer GACTCCACGACGTACTCAGC (SEQ ID NO. 4); Rat MCP1 forward primer CTTCCAAGTGGCTAAGGGCA (SEQ ID NO. 5), reverse primer TCAAAGGGAGTCGGG-GATCT (SEQ ID NO. 6); Rat TNFα forward primer GATCGGTCCCAACAAGGAGG (SEQ ID NO. 7), reverse primer TCCCTCAGGGGTGTCCTTAG (SEQ ID NO. 8); Rat BAX forward primer CACTAAAGTGCCCGAGCTGA (SEQ ID NO. 9), reverse primer TCCAGATGGTGAGT-GAGGCA (SEQ ID NO. 10); Rat Caspase3 forward primer ACTGGAATGTCAGCTCGCAA (SEQ ID NO. 11), reverse primer TCAAATTCCGTGGCCACCTT (SEQ ID NO. 12); Rat GAPDH forward primer GACATGCCGCCTG-GAGAAAC (SEQ ID NO. 13), reverse primer AGCCCAG-GATGCCCTTTAGT (SEQ ID NO. 14).

Statistical Analysis. All data are presented as mean±standard error of the mean (SEM). Statistical analysis was performed using GraphPad Prism 9.1.0. For multiple group-wise comparison, one-way analysis of variance (ANOVA) was performed followed by Bonferroni post-hoc tests. For two-group comparison, Student's t-test was performed. The value $P < 0.05$ was considered to be statistically significant.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

REFERENCES

1. Alexander, M. R.; et al. Epigenetic control of smooth muscle cell differentiation and phenotypic switching in vascular development and disease. Annu. Rev. Physiol. 2012, 74, 13-40.
2. Ang, H. Y.; et al. Adventitial injection delivery of nano-encapsulated sirolimus (Nanolimus) to injury-induced porcine femoral vessels to reduce luminal restenosis. J. Control. Release 2020, 319, 15-24.
3. Anselmo, A. C.; et al. Nanoparticles in the clinic: An update. Bioengineering & Translational Medicine 2019, 4.
4. Bahnson, E. S. M.; et al. Targeted Nitric Oxide Delivery by Supramolecular Nanofibers for
5. Banai, S.; et al. Targeted anti-inflammatory systemic therapy for restenosis: The Biorest Liposomal Alendronate with Stenting sTudy (BLAST)—a double blind, randomized clinical trial. Am. Heart J. 2013, 165, 234-240.
6. Barua, S.; et al. Challenges associated with penetration of nanoparticles across cell and tissue barriers: A review of current status and future prospects. Nano Today 2014, 9, 223-243.
7. Cassese, S.; et al. Incidence and predictors of restenosis after coronary stenting in 10 004 patients with surveillance angiography. Heart 2013, 100, 153-159.
8. Chan, J. M.; et al. In vivo prevention of arterial restenosis with paclitaxel-encapsulated targeted lipid-polymeric nanoparticles. Proceedings of the National Academy of Sciences 2011, 108, 19347-19352.
9. de Gracia Lux, C.; et al. Biocompatible Polymeric Nanoparticles Degrade and Release Cargo in Response to Biologically Relevant Levels of Hydrogen Peroxide. J. Am. Chem. Soc. 2012, 134, 15758-15764.
10. Fang, R. H.; et al. Cell Membrane Coating Nanotechnology. Adv. Mater. 2018, 30, 1706759.
11. Feng, L.; et al. Enhancement of Nanozyme Permeation by Endovascular Interventional Treatment to Prevent Vascular Restenosis via Macrophage Polarization Modulation. Adv. Funct. Mater. 2020, 30, 2006581.
12. Feng, S.; et al. Nanoparticles responsive to the inflammatory microenvironment for targeted treatment of arterial restenosis. Biomaterials 2016, 105, 167-184.
13. Ghosh, G. C.; et al. RVX 208: A novel BET protein inhibitor, role as an inducer of apo A-I/HDL and beyond. Cardiovasc. Ther. 2017, 35, e12265.
14. Gilham, D.; et al. RVX-208, a BET-inhibitor for treating atherosclerotic cardiovascular disease, raises ApoA-I/HDL and represses pathways that contribute to cardiovascular disease. Atherosclerosis 2016, 247, 48-57.

15. Haeri, A.; et al. Effective attenuation of vascular restenosis following local delivery of chitosan decorated sirolimus liposomes. Carbohyd. Polym. 2017, 157, 1461-1469.

16. Hajibandeh, S.; et al. Treatment strategies for in-stent restenosis in peripheral arterial disease: a systematic review. Interact. Cardiov. Th. 2019, 28, 253-261.

17. Hoshyar, N.; et al. The effect of nanoparticle size on in vivo pharmacokinetics and cellular interaction. Nano-medicine-UK 2016, 11, 673-692.

18. Hu, C. J.; et al. Nanoparticle biointerfacing by platelet membrane cloaking. Nature 2015, 526, 118-121.

19. Hu, Q.; et al. Anticancer Platelet-Mimicking Nanovehicles. Adv. Mater. 2015, 27, 7043-7050.

20. Inoue, T.; et al. Vascular Inflammation and Repair: implications for re-endothelialization, restenosis, and stent thrombosis. JACC: Cardiovascular Interventions 2011, 4, 1057-1066.

21. Islam, M. A.; et al. A multiscale modeling study of particle size effects on the tissue penetration efficacy of drug-delivery nanoparticles. BMC Syst. Biol. 2017, 11.

22. Iyer, R.; et al. Nanoparticle eluting-angioplasty balloons to treat cardiovascular diseases. Int. J. Pharmaceut. 2019, 554, 212-223.

23. Jahagirdar, R.; et al. A novel BET bromodomain inhibitor, RVX-208, shows reduction of atherosclerosis in hyperlipidemic ApoE deficient mice. Atherosclerosis 2014, 236, 91-100.

24. Jung, S. M.; et al. Platelet Glycoprotein VI. Adv. Exp. Med. Biol. 2008, 640, 53-63.

25. Katsanos, K.; et al. Risk of Death Following Application of Paclitaxel-Coated Balloons and Stents in the Femoro-popliteal Artery of the Leg: A Systematic Review and Meta-Analysis of Randomized Controlled Trials. J. Am. Heart Assoc. 2018, 7.

26. Khoobchandani, M.; et al. Laminin Receptor-Avid Nanotherapeutic EGCg-AuNPs as a Potential Alternative Therapeutic Approach to Prevent Restenosis. Int. J. Mol. Sci. 2016, 17, 316.

27. Li, L.; et al. Synthesis and characterization of dendritic star-shaped zwitterionic polymers as novel anticancer drug delivery carriers. J Biomater Sci Polym Ed 2014, 25, 1641-1657.

28. Liu, X.; et al. Fusogenic Reactive Oxygen Species Triggered Charge-Reversal Vector for Effective Gene Delivery. Adv. Mater. 2016, 28, 1743-1752.

29. Lüscher, T. F.; et al. Drug-Eluting Stent and Coronary Thrombosis: biological mechanisms and clinical implications. Circulation 2007, 115, 1051-1058.

30. Margolis, J.; et al. Systemic Nanoparticle Paclitaxel (nab-Paclitaxel) for In-stent Restenosis I (SNAPIST-1): A First-in-Human Safety and Dose-finding Study. Clin. Cardiol. 2007, 30, 165-170.

31. Mills, B.; et al. Intimal hyperplasia: slow but deadly. Perfusion 2012, 27, 520-528.

32. Myerson, J. W.; et al. Non-affinity factors modulating vascular targeting of nano- and microcarriers. Adv. Drug Deliver. Rev. 2016, 99, 97-112.

33. Nicholls, S. J.; et al. Apabetalone and hospitalization for heart failure in patients following an acute coronary syndrome: a prespecified analysis of the BETonMACE study. Cardiovasc. Diabetol. 2021, 20.

34. Park, J. H.; et al. Biomimetic nanoparticle technology for cardiovascular disease detection and treatment. Nanoscale Horiz 2020, 5, 25-42.

35. Picaud, S.; et al. RVX-208, an inhibitor of BET transcriptional regulators with selectivity for the second bromodomain. Proceedings of the National Academy of Sciences 2013, 110, 19754-19759.

36. Pires, N.; et al. Histopathologic alterations following local delivery of dexamethasone to inhibit restenosis in murine arteries. Cardiovasc. Res. 2005, 68, 415-424.

37. Secretariat, M. A. Stenting for Peripheral Artery Disease of the Lower Extremities: an evidence-based analysis. Ont Health Technol Assess Ser 2010, 10, 1-88.

38. Shen, D.; et al. (PtBA-co-PPEGMEMA-co-PDOMA)-g-PPFA polymer brushes synthesized by sequential RAFT polymerization and ATRP. Polym. Chem.—UK 2018, 9, 2821.

39. Stampfl, U.; et al. Paclitaxel-induced Arterial Wall Toxicity and Inflammation: Part 2-Long-term Tissue Response in a Minipig Model. J. Vasc. Interv. Radiol. 2009, 20, 1608-1616.

40. Tannock, I. F.; et al. Limited penetration of anticancer drugs through tumor tissue: a potential cause of resistance of solid tumors to chemotherapy. Clin. Cancer Res. 2002, 8, 878-884.

41. Tee, J. K.; et al. Nanoparticles' interactions with vasculature in diseases. Chem. Soc. Rev. 2019, 48, 5381-5407.

42. Thukkani, A. K.; et al. Endovascular Intervention for Peripheral Artery Disease. Circ. Res. 2015, 116, 1599-1613.

43. Varshosaz, J.; et al. Magnetic chondroitin targeted nanoparticles for dual targeting of montelukast in prevention of in-stent restenosis. RSC Adv. 2016, 6, 12337-12347.

44. Wang, B.; et al. A paradigm of endothelium-protective and stent-free anti-restenotic therapy using biomimetic nanoclusters. Biomaterials 2018, 178, 293-301.

45. Wang, B.; et al. BET Bromodomain Blockade Mitigates Intimal Hyperplasia in Rat Carotid Arteries. EBioMedicine 2015, 2, 1650-1661.

46. Wang, B.; et al. PERK Inhibition Promotes Post-angioplasty Re-endothelialization via Modulating SMC Phenotype Changes. J. Surg. Res. 2021, 257, 294-305.

47. Wang, S.; et al. Drug Targeting via Platelet Membrane-Coated Nanoparticles. Small Structures 2020, 1, 2000018.

48. Wang, Y.; et al. *Cordyceps sinensis* polysaccharide inhibits PDGF-BB-induced inflammation and ROS production in human mesangial cells. Carbohyd. Polym. 2015, 125, 135-145.

49. Wasiak, S.; et al. BET protein inhibitor apabetalone (RVX-208) suppresses pro-inflammatory hyper-activation of monocytes from patients with cardiovascular disease and type 2 diabetes. Clin. Epigenetics 2020, 12.

50. Welt, F. G. P.; et al. Inflammation and Restenosis in the Stent Era. Arteriosclerosis, Thrombosis, and Vascular Biology 2002, 22, 1769-1776.

51. Wykrzykowska, J. J.; et al. Bioresorbable scaffolds versus metallic stents in routine PCI. New Engl. J. Med. 2017, 376, 2319-2328.

52. Yan, H.; et al. Engineering Cell Membrane-Based Nanotherapeutics to Target Inflammation. Advanced Science 2019, 6, 1900605.

53. Zein, R.; et al. Physical Properties of Nanoparticles That Result in Improved Cancer Targeting. Journal of Oncology 2020, 2020, 1-16.

54. Zhang, M.; et al. The BD2 domain of BRD4 is a determinant in EndoMT and vein graft neointima formation. Cell. Signal. 2019, 61, 20-29.

55. Zhang, R.; et al. A pH/ROS dual-responsive and targeting nanotherapy for vascular inflammatory diseases. Biomaterials 2020, 230, 119605.

56. Zhao, Y.; et al. Biomimetic fibrin-targeted and H2O2-responsive nanocarriers for thrombus therapy. Nano Today 2020, 35, 100986.

57. Zhao, Y.; et al. Co-delivery of LOX-1 siRNA and statin to endothelial cells and macrophages in the atherosclerotic lesions by a dual-targeting core-shell nanoplatform: A dual cell therapy to regress plaques. J. Control. Release 2018, 283, 241-260.

58. Zhao, Y.; et al. Multifunctional Dextran Sulfate-Coated Reconstituted High Density Lipoproteins Target Macrophages and Promote Beneficial Antiatherosclerotic Mechanisms. Bioconjugate Chem. 2016, 28, 438-448.

What is claimed is:

1. A nanocluster comprising:

(a) a core comprising self-assembled unimolecular nanoparticles, wherein the core, upon exposure to at least one reactive oxygen species (ROS), disassembles back into unimolecular nanoparticles;

(b) a biomimetic membrane coating surrounding the core; and (c) a block copolymer comprising units derived from a lactide monomer, wherein the block copolymer comprises H40-polylactide-block-poly{methacrylic acid-ran-2-(methacryloyloxy)-N,N-dimethyl-N-[4-(4,4,5,5-tetramethyl-1,3,2-dioxaborolan-2-yl)benzyl]ethan-1-aminium}.

2. The nanocluster of claim 1, wherein the biomimetic membrane comprises a platelet-derived membrane, a macrophage-derived membrane, a leukocyte-derived membrane, a mesenchymal stem cell-derived membrane, an exosomal membrane, a liposomal membrane, or any combination thereof.

3. The nanocluster of claim 1, wherein the unimolecular nanoparticles comprise a hydrophobic group, wherein the hydrophobic group comprises a phenylboronic ester.

4. The nanocluster of claim 1, wherein the biomimetic membrane coating is derived from human cells, exosomes, or liposomes.

5. The nanocluster of claim 4, wherein the human cells comprise platelets, macrophages, leukocytes, mesenchymal stem cells, endothelial cells, or endothelial progenitor cells.

6. The nanocluster of claim 1, further comprising a drug, wherein the drug comprises an anti-restenotic drug.

7. The nanocluster of claim 6, wherein the anti-restenotic drug comprises RVX-208, RVX-297, resveratrol, JQ1, OTX-015, ZEN-3694, I-BET762, ABBV-744, ARV-825, sirolimus, everolimus, tacrolimus, paclitaxel, GCN2-IN-1, GSK2606414, GSK2656157, halofuginone, CI-amidine, D-CI-amidine, CI4-amidine, CAY10723, GSK484, EZP-6438, A-395, EED226, tubastatin, SIS3, centrinone B, or any combination thereof.

8. The nanocluster of claim 1, wherein the unimolecular nanoparticles have an average diameter of from about 10 to 70 nm.

9. A nanocluster composition comprising a plurality of individual nanoclusters according to claim 3.

10. The nanocluster composition of claim 9, wherein the individual nanoclusters have an average diameter of from about 100 to 250 nm.

11. A method for treating at least one vascular damage event in a subject, the method comprising administering the nanocluster composition of claim 9 to a subject.

12. The method of claim 11, wherein the biomimetic membrane localizes the nanoclusters at one or more sites of vascular damage in the subject.

13. The method of claim 11, wherein the at least one vascular damage event comprises restenosis, aneurysm, deep vein thrombosis, or any combination thereof.

14. The method of claim 11, wherein administering the nanocluster composition comprises intravenous injection of a unit dose of the nanocluster composition.

15. The method of claim 14, wherein the unit dose of the nanocluster composition comprises from about 5 to about 50 mg of a drug per kg of body weight of the subject.

16. The method of claim 15, wherein the drug comprises RVX-208, RVX-297, resveratrol, JQ1, OTX-015, ZEN-3694, I-BET762, ABBV-744, ARV-825, sirolimus, everolimus, tacrolimus, paclitaxel, GCN2-IN-1, GSK2606414, GSK2656157, halofuginone, CI-amidine, D-CI-amidine, CI4-amidine, CAY10723, GSK484, EZP-6438, A-395, EED226, tubastatin, SIS3, centrinone B, or any combination thereof.

17. The method of claim 11, wherein one or more reactive oxygen species at the one or more sites of vascular damage cleaves the hydrophobic end group, wherein cleavage of the hydrophobic end group triggers release of one or more water soluble byproducts and a transition of the unimolecular nanoparticles to hydrophilic nanoparticles.

* * * * *